US012116421B2

(12) United States Patent
Hauser et al.

(10) Patent No.: US 12,116,421 B2
(45) Date of Patent: Oct. 15, 2024

(54) PEPTIDE-BASED DOPA CONTAINING ADHESIVE GELS

(71) Applicant: KING ABDULLAH UNIVERSITY OF SCIENCE AND TECHNOLOGY, Thuwal (SA)

(72) Inventors: Charlotte A. E. Hauser, Thuwal (SA); Maria Hountondji, Thuwal (SA); Manola Moretti, Thuwal (SA); Panagiotis Bilalis, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 18/021,645

(22) PCT Filed: Sep. 2, 2021

(86) PCT No.: PCT/IB2021/057996
§ 371 (c)(1),
(2) Date: Feb. 16, 2023

(87) PCT Pub. No.: WO2022/049508
PCT Pub. Date: Mar. 10, 2022

(65) Prior Publication Data
US 2023/0374069 A1 Nov. 23, 2023

Related U.S. Application Data

(60) Provisional application No. 63/073,505, filed on Sep. 2, 2020.

(51) Int. Cl.
*C07K 7/06* (2006.01)
*C12N 5/00* (2006.01)
*C12N 5/07* (2010.01)

(52) U.S. Cl.
CPC .............. *C07K 7/06* (2013.01); *C12N 5/0062* (2013.01); *C12N 5/0601* (2013.01); *C12N 2513/00* (2013.01); *C12N 2533/50* (2013.01)

(58) Field of Classification Search
None
See application file for complete search history.

(56) References Cited

U.S. PATENT DOCUMENTS

| | | |
|---|---|---|
| 2003/0175410 A1 | 9/2003 | Campbell et al. |
| 2007/0154552 A1 | 7/2007 | Siegal et al. |
| 2008/0095748 A1 | 4/2008 | Kharazi et al. |
| 2011/0008293 A1 | 1/2011 | Bhandari |
| 2014/0012225 A1 | 1/2014 | Yoo et al. |
| 2015/0038428 A1 | 2/2015 | Hauser et al. |
| 2016/0288414 A1 | 10/2016 | Ozbolat et al. |
| 2017/0056548 A1 | 3/2017 | Lee et al. |
| 2018/0118978 A1 | 5/2018 | Yabu et al. |
| 2020/0148720 A1 | 5/2020 | Hauser et al. |
| 2020/0199514 A1 | 6/2020 | Hauser et al. |
| 2022/0054706 A1 | 2/2022 | Hauser et al. |
| 2022/0371958 A1* | 11/2022 | Hauser .............. E02B 3/046 |
| 2023/0295225 A1 | 9/2023 | Hauser et al. |
| 2023/0405177 A1 | 12/2023 | Hauser et al. |

FOREIGN PATENT DOCUMENTS

| | | |
|---|---|---|
| CN | 105 881 908 A | 8/2016 |
| JP | 2013 009598 A | 1/2013 |
| KR | 2016 0091993 A | 8/2016 |
| KR | 10-2020-0007537 A | 1/2020 |
| KR | 10-2021-0104339 A | 8/2021 |
| WO | 2007/102735 A1 | 9/2007 |
| WO | 2008/057608 A1 | 5/2008 |
| WO | 2008/057608 A2 | 5/2008 |
| WO | 2014/104981 A1 | 7/2014 |
| WO | 2014/197999 A1 | 12/2014 |
| WO | 2015/080671 A1 | 6/2015 |
| WO | 2016/144259 A1 | 9/2016 |
| WO | 2018/207036 A1 | 11/2018 |
| WO | 2018/207037 A1 | 11/2018 |
| WO | 2020/162835 A1 | 8/2020 |

OTHER PUBLICATIONS

Zhang et al., "Catechol functionalized hyperbranched polymers as biomedical materials", Polymers in Polymer Science, vol. 78, pp. 47-55 (2018).
Examination Report received in Saudi Arabian Application No. 523442624 mailed Sep. 28, 2023.
International Search Report and Written Opinion received in PCT Application No. PCT/IB2023/056328 mailed Oct. 13, 2023.
Search Report and Written Opinion received in PCT Application No. PCT/IB2021/057996 mailed Dec. 20, 2021.
R. Pérez-Pedroza, A. Ávila-Ramirez, Z. Khan, M. Moretti, C. A. E. Hauser, Advances in Polymer Technology 2021, 2021, 8815006.
S. Abdelrahman, M. Alghrably, J. I. Lachowicz, A.-H. Emwas, C. A. E. Hauser, M. Jaremko, Molecules 2020, 25.
A. P. Duarte, J. F. Coelho, J. C. Bordado, M. T. Cidade, M. H. Gil, Progress in Polymer Science 2012, 37, 1031-1050.
H. Zhu, J. Tian, H. Mao, Z. Gu, Current Opinion in Biomedical Engineering 2021, 18, 100271.
C. A. Hauser, R. Deng, A. Mishra, Y. Loo, U. Khoe, F. Zhuang, D. W. Cheong, A. Accardo, M. B. Sullivan, C. Riekel, J. Y. Ying, U. A. Hauser, Proc Natl Acad Sci U S A 2011, 108, 1361-1366.
N. Wiradharma, U. Khoe, C. A. E. Hauser, S. V. Seow, S. Zhang, Y.-Y. Yang, Biomaterials 2011, 32, 2204-2212.

(Continued)

*Primary Examiner* — Sudhakar Katakam
*Assistant Examiner* — Zachary J Miknis
(74) *Attorney, Agent, or Firm* — Ajay A. Jagtiani; Miles & Stockbridge P.C.

(57) ABSTRACT

The present disclosure relates to Dopa containing ultrashort peptides capable of forming a gel, to a gel comprising a peptide in accordance with the present disclosure, and to a glue comprising a peptide in accordance with the present disclosure. Such gel is adhesive and is biocompatible. The peptides are suitable for building 3D structures, 3D printing, gluing as well as other applications.

22 Claims, 21 Drawing Sheets

Specification includes a Sequence Listing.

(56) References Cited

OTHER PUBLICATIONS

E. C. Wu, S. Zhang, C. A. E. Hauser, Advanced Functional Materials 2012, 22, 456-468.
Y. Loo, Y.-C. Wong, E. Z. Cai, C.-H. Ang, A. Raju, A. Lakshmanan, A. G. Koh, H. J. Zhou, T.-C. Lim, S. M. Moochhala, C. A. E. Hauser, Biomaterials 2014, 35, 4805-4814.
Y. Loo, M. Goktas, A. B. Tekinay, M. O. Guler, C. A. Hauser, A. Mitraki, Adv Healthc Mater 2015, 4, 2557-2586.
Y. Loo, Y. S. Chan, I. Szczerbinska, B. C. P. Tan, A. C. A. Wan, H. H. Ng, C. A. E. Hauser, ACS Applied Bio Materials 2019, 2, 1406-1412.
H. H. Susapto, D. Alhattab, S. Abdelrahman, Z. Khan, S. Alshehri, K. Kahin, R. Ge, M. Moretti, A.-H. Emwas, C. A. E. Hauser, Nano Letters 2021, 21, 2719-2729.
W. Arab, C. A. E. Hauser, in Peptide-based Biomaterials, The Royal Society of Chemistry, 2021, pp. 363-394.
K. Autumn, Y. A. Liang, S. T. Hsieh, W. Zesch, W. P. Chan, T. W. Kenny, R. Fearing, R. J. Full, Nature 2000, 405, 681-685.
M. D. Bartlett, A. B. Croll, D. R. King, B. M. Paret, D. J. Irschick, A. J. Crosby, Advanced Materials 2012, 24, 994-994.
R. J. Stewart, T. C. Ransom, V. Hlady, J Polym Sci B Polym Phys 2011, 49, 757-771.
A. Hagenau, M. H. Suhre, T. R. Scheibel, Progress in Polymer Science 2014, 39, 1564-1583.
J. Yu, W. Wei, E. Danner, R. K. Ashley, J. N. Israelachvili, J. H. Waite, Nature Chemical Biology 2011, 7, 588-590.
A. F. Dexter, A. S. Malcolm, A. P. Middelberg, Nat Mater 2006, 5, 502-506.
M. de Loos, B. L. Feringa, J. H. van Esch, European Journal of Organic Chemistry 2005, 2005, 3615-3631.
X. Yan, D. Xu, X. Chi, J. Chen, S. Dong, X. Ding, Y. Yu, F. Huang, Adv Mater 2012, 24, 362-369.
M. Ikeda, T. Tanida, T. Yoshii, I. Hamachi, Advanced Materials 2011, 23, 2819-2822.
T. Aida, E. W. Meijer, S. I. Stupp, Science 2012, 335, 813-817.
H. Lee, S. M. Dellatore, W. M. Miller, P. B. Messersmith, Science (New York, N.Y.) 2007, 318, 426-430.
Q. Lin, D. Gourdon, C. Sun, N. Holten-Andersen, T. H. Anderson, J. H. Waite, J. N. Israelachvili, Proc Natl Acad Sci U S A 2007, 104, 3782-3786.
J. D. White, J. J. Wilker, Macromolecules 2011, 44, 5085-5088.
H. Zhao, J. H. Waite, J Biol Chem 2006, 281, 26150-26158.
M. V. Rapp, G. P. Maier, H. A. Dobbs, N. J. Higdon, J. H. Waite, A. Butler, J. N. Israelachvili, Journal of the American Chemical Society 2016, 138, 9013-9016.
M. Shin, J. Y. Shin, K. Kim, B. Yang, J. W. Han, N.-K. Kim, H. J. Cha, Journal of Colloid and Interface Science 2020, 563, 168-176.
J. Yang, M. A. Cohen Stuart, M. Kamperman, Chemical Society Reviews 2014, 43, 8271-8298.
B. K. Ahn, S. Das, R. Linstadt, Y. Kaufman, N. R. Martinez-Rodriguez, R. Mirshafian, E. Kesselman, Y. Talmon, B. H. Lipshutz, J. N. Israelachvili, J. H. Waite, Nature Communications 2015, 6, 8663-8663.
M. Krogsgaard, M. A. Behrens, J. S. Pedersen, H. Birkedal, Biomacromolecules 2013, 14, 297-301.
Q. Zhao, D. W. Lee, B. K. Ahn, S. Seo, Y. Kaufman, J. N. Israelachvili, J. H. Waite, Nat Mater 2016, 15, 407-412.
Q. Zhao, D. W. Lee, B. K. Ahn, S. Seo, Y. Kaufman, Jacob N. Israelachvili, J. H. Waite, Nature Materials 2016, 15, 407-412.
J. Li, A. D. Celiz, J. Yang, Q. Yang, I. Wamala, W. Whyte, B. R. Seo, N. V. Vasilyev, J. J. Vlassak, Z. Suo, D. J. Mooney, Science 2017, 357, 378-381.
Y. Shou, J. Zhang, S. Yan, P. Xia, P. Xu, G. Li, K. Zhang, J. Yin, ACS Biomaterials Science & Engineering 2020, 6, 3619-3629.
L. Han, X. Lu, K. Liu, K. Wang, L. Fang, L.-T. Weng, H. Zhang, Y. Tang, F. Ren, C. Zhao, G. Sun, R. Liang, Z. Li, ACS Nano 2017, 11, 2561-2574.
Y. Zhou, L. Kang, Z. Yue, X. Liu, G. G. Wallace, ACS Applied Bio Materials 2020, 3, 628-638.
C. E. Brubaker, H. Kissler, L.-J. Wang, D. B. Kaufman, P. B. Messersmith, Biomaterials 2010, 31, 420-427.
R. Wang, J. Li, W. Chen, T. Xu, S. Yun, Z. Xu, Z. Xu, T. Sato, B. Chi, H. Xu, Advanced Functional Materials 2017, 27, 1604894.
C. J. Kastrup, M. Nahrendorf, J. L. Figueiredo, H. Lee, S. Kambhampati, T. Lee, S.-W. Cho, R. Gorbatov, Y. Iwamoto, T. T. Dang, P. Dutta, J. H. Yeon, H. Cheng, C. D. Pritchard, A. J. Vegas, C. D. Siegel, S. MacDougall, M. Okonkwo, A. Thai, J. R. Stone, A. J. Coury, R. Weissleder, R. Langer, D. G. Anderson, Proceedings of the National Academy of Sciences 2012, 109, 21444-21449.
L. Zhang, M. Liu, Y. Zhang, R. Pei, Biomacromolecules 2020, 21, 3966-3983.
F. Pan, S. Ye, R. Wang, W. She, J. Liu, Z. Sun, W. Zhang, Materials Horizons 2020, 7, 2063-2070.
B. D. B. Tiu, P. Delparastan, M. R. Ney, M. Gerst, P. B. Messersmith, ACS Appl Mater Interfaces 2019, 11, 28296-28306.
Y. Li, J. Cheng, P. Delparastan, H. Wang, S. J. Sigg, K. G. DeFrates, Y. Cao, P. B. Messersmith, Nature Communications 2020, 11, 3895.
M. Moretti, C. Canale, M. Francardi, S. Dante, F. De Angelis, E. Di Fabrizio, Microsc Res Tech 2012, 75, 1723-1731.
M. Moretti, R. La Rocca, M. Perrone Donnorso, B. Torre, C. Canale, M. Malerba, G. Das, R. Sottile, C. Garofalo, A. Achour, K. Kärre, E. Carbone, E. Di Fabrizio, ACS Nano 2021, 15, 7500-7512.
Y. Loo, A. Lakshmanan, M. Ni, L. L. Toh, S. Wang, C. A. Hauser, Nano Lett 2015, 15, 6919-6925.
J. L. Hutter, J. Bechhoefer, Journal of Vacuum Science & Technology B: Microelectronics and Nanometer Structures Processing, Measurement, and Phenomena 1994, 12, 2251-2253.
A. L. Weisenhorn, P. K. Hansma, T. R. Albrecht, C. F. Quate, Applied Physics Letters 1989, 54, 2651-2653.
H. R. Nelson, A. H. Altieri, Coral Reefs 2019, 38, 177-198.
S. Schmidt-Roach, C. M. Duarte, C. A. E. Hauser, M. Aranda, Frontiers in Marine Science 2020, 7.
D. W. dela Cruz, B. Rinkevich, E. D. Gomez, H. T. Yap, Ecological Engineering 2015, 84, 408-415.
S. A. Schopmeyer, D. Lirman, E. Bartels, D. S. Gilliam, E. A. Goergen, S. P. Griffin, M. E. Johnson, C. Lustic, K. Maxwell, C. S. Walter, Coral Reefs 2017, 36, 1047-1057.
J. L. Hutter, J. Bechhoefer, Review of Scientific Instruments 1993, 64, 1868-1873.
W. L. Jorgensen, J. Tirado-Rives, Proceedings of the National Academy of Sciences of the United States of America 2005, 102, 6665-6670.
M. J. Abraham, T. Murtola, R. Schulz, S. Páll, J. C. Smith, B. Hess, E. Lindahl, SoftwareX 2015, 1-2, 19-25.
L. S. Dodda, I. Cabeza de Vaca, J. Tirado-Rives, W. L. Jorgensen, Nucleic Acids Research 2017, 45, W331-W336.
T. Darden, D. York, L. Pedersen, The Journal of Chemical Physics 1993, 98, 10089-10092.
H. J. C. Berendsen, J. P. M. Postma, W. F. v. Gunsteren, A. DiNola, J. R. Haak, The Journal of Chemical Physics 1984, 81, 3684-3690.
G. Bussi, D. Donadio, M. Parrinello, The Journal of Chemical Physics 2007, 126, 014101.
Y. J. Choi, Y. J. Jun, D. Y. Kim, H. G. Yi, S. H. Chae, J. Kang, J. Lee, G. Gao, J. S. Kong, J. Jang, W. K. Chung, J. W. Rhie, D. W. Cho, Biomaterials 2019, 206, 160-169.
A. Micsonai, F. Wien, É. Bulyáki, J. Kun, É. Moussong, Y.-H. Lee, Y. Goto, M. Réfrégiers, J. Kardos, Nucleic Acids Research 2018, 46, W315-W322.
W. Kabsch, C. Sander, Biopolymers 1983, 22, 2577-2637.
N. J. Greenfield, Nat Protoc 2006, 1, 2876-2890.
Written Opinion received in Singapore Application No. 10202112455P dated Jul. 11, 2023.
Office Action received in Japanese Application No. 2019-561848 dated May 22, 2023.
Notice of Final Rejection received in Korean Application No. 10-2019-7036272 dated May 25, 2023.
European Search Report received in European Application No. 23159765.9 dated Jun. 22, 2023.
Ali et al., "A Non-Canonical NRPS Is Involved in the Synthesis of Fungisporin and Related Hydrophobic Cyclic Tetrapeptides in Penicillium chrysogenum", PLOS One; vol. 9, Issue 6, e98212 (2014).
Pubchem CID: 93078 "L-Aspartyl-L_phenylalanine" (2005).

(56) References Cited

OTHER PUBLICATIONS

Vasco et al., "Macrocyclization of Peptide Side Chains by the Ugi Reaction: Achieving Peptide Folding and Exocyclic N-Functionalization in One Shot", The Journal of Organic Chemistry, 80, pp. 6697-6707 (2015).
Official Action received in Japanese Application No. 2019-561848 dated Feb. 28, 2023.
Decision of Dismissal of Amendment received in Japanese Application No. 2019-561747 mailed Apr. 18, 2023.
Liu et al., "Stiffness-mediated mesenchymal stem cell fate decision in 3D-bioprinted hydrogels", Burns & Trauma, vol. 8 (2020).
Written Opinion received in Singapore Application No. 1020112455P dated Mar. 27, 2024.
Examination Report received in Saudi Arabian Application No. 523442596 dated Mar. 31, 2024.
Non-Final Office Action received in U.S. Appl. No. 18/021,645 dated Apr. 1, 2024.
Pubchem CID: 97078 "L-Aspartyl-L-phenylalanine".

* cited by examiner

DoIIZK  IIZDoK

IIZKDo  IIZ(KDo)$_2$  IIZ(KDo)$_3$

|  | DoIIZK | IIZDoK | IIZKDo |
|---|---|---|---|
| 1 mg/ml | Not gelating | Not gelating | Not gelating |
| 2 mg/ml | > 45 min  | Not gelating | Not gelating |
| 3 mg/ml | > 30 min  | Not gelating | > 30 min  |
| 4 mg/ml | > 20 min  | > 80 min  | >21 min  |
| 5 mg/ml | > 10 min  | > 75 min  | >16 min  | ns

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Levodopa
<220> FEATURE:
<221> NAME/KEY: SITE
<222> LOCATION: (3)..(3)
<223> OTHER INFORMATION: Xaa is Cyclohexylalanine
```

<400> SEQUENCE: 1

Ile Ile Xaa Lys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Levodopa
<220> FEATURE:
<221> NAME/KEY: SITE
<222> LOCATION: (3)..(3)
<223> OTHER INFORMATION: Xaa is Cyclohexylalanine

<400> SEQUENCE: 2

Ile Ile Xaa Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (3)..(3)
<223> OTHER INFORMATION: Xaa is Cyclohexylalanine
<220> FEATURE:
<221> NAME/KEY: MOD_RES
<222> LOCATION: (4)..(4)
<223> OTHER INFORMATION: Levodopa

<400> SEQUENCE: 3

Ile Ile Xaa Lys
1

<210> SEQ ID NO 4
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (3)..(3)
<223> OTHER INFORMATION: Xaa is Cyclohexylalanine
<220> FEATURE:
<221> NAME/KEY: MOD_RES
<222> LOCATION: (4)..(4)
<223> OTHER INFORMATION: Levodopa
<220> FEATURE:
<221> NAME/KEY: MOD_RES
<222> LOCATION: (5)..(5)
<223> OTHER INFORMATION: Levodopa

<400> SEQUENCE: 4

Ile Ile Xaa Lys Lys
1               5

<210> SEQ ID NO 5
<211> LENGTH: 6
<212> TYPE: PRT
<213> ORGANISM: Artificial Sequence
<220> FEATURE:

```
<223> OTHER INFORMATION: Synthetic
<220> FEATURE:
<221> NAME/KEY: SITE
<222> LOCATION: (3)..(3)
<223> OTHER INFORMATION: Xaa is Cyclohexylalanine
<220> FEATURE:
<221> NAME/KEY: MOD_RES
<222> LOCATION: (4)..(4)
<223> OTHER INFORMATION: Levodopa
<220> FEATURE:
<221> NAME/KEY: MOD_RES
<222> LOCATION: (5)..(5)
<223> OTHER INFORMATION: Levodopa
<220> FEATURE:
<221> NAME/KEY: MOD_RES
<222> LOCATION: (6)..(6)
<223> OTHER INFORMATION: Levodopa

<400> SEQUENCE: 5

Ile Ile Xaa Lys Lys Lys
1               5
```

PEPTIDE-BASED DOPA CONTAINING ADHESIVE GELS

CROSS-REFERENCE TO RELATED APPLICATIONS

This application claims benefit of priority of U.S. Provisional Patent Application No. 63/073,505 entitled, "PEPTIDE-BASED ADHESIVE MATERIALS" filed Sep. 2, 2020. The entire contents and disclosures of these patent applications are incorporated herein by reference in their entirety.

REFERENCE TO A "SEQUENCE LISTING"

The present application includes a Sequence Listing which has been submitted electronically in an ASCII text format. This Sequence Listing is named 114147-23829WO01_sequence listing.TXT was created on Aug. 16, 2021, is 1,839 bytes in size and is hereby incorporated by reference in its entirety.

BACKGROUND

Field of the Invention

The present disclosure relates to peptides capable of forming a gel. The present disclosure further relates to a gel comprising a peptide containing Dopa moiety in accordance with the present disclosure, to a glue comprising a peptide in accordance with the present disclosure.

Background of the Invention

Hydrogels based on ultrashort self-assembling peptides (SAPs) are an intriguing alternative to collagen-mimicking matrices extracted from tissue, due to the low immunogenicity, high biocompatibility and biodegradability, and tunable mechanical properties of the ultrashort SAPs.[1-2] SAP hydrogels properties can be tuned by easy modification of their sequence, or addition of desirable moieties.

Wet adhesion materials that are biocompatible/biodegradable, environmentally friendly, and preserve proper mechanical properties are needed both in the medical field and in underwater adhesion. Commonly used glues in the medical and field include cyanoacrylate based glues and fibrin based glues. However, both of these materials have their drawbacks. For instance, cyanoacrylate based glues are toxic and with poor mechanical properties, while fibrin based glues increase the chances of infection and are available only in small volumes.[3-4] Common glues for underwater engineering or environmental applications are based likewise on acrylate chemistry. Instead, wet adhesives based on hydrogels are highly attractive due to their capability to resemble the extracellular environment and being biodegradable. In particular, SAP peptides have proven high biocompatibility, mechanical stability and tunability, and antibacterial properties.[5-11]

In addition, the potential of SAP peptides for wound healing and skin grafts has been validated.[12] Because of their already demonstrated excellent properties, improvement of their adhesiveness in wet conditions is desirable.

Efficient underwater adhesion for hydrogels is often hindered by the high dielectric and ionic strength of physiological fluids and marine environments. Notwithstanding, the wet adhesion of the catechol group to a variety of substrates in the presence of ionic species is well-documented. Glue from caddisfly larva, mussels and oysters, barnacle cements, kelp adhesives, (lizards such as geckos) and tube worms are some examples of natural gluing materials.[13-22] Promiscuous fouling organisms and fascinating species have mastered the ability to attach themselves, by extending hair-like fibers, to virtually all types of existing inorganic and organic surfaces, —to survive in their turbulent, saline and wet habitat—by their byssus. These environment-tolerant bioadhesive proteins are supported by protein-based adhesive mussels produce, such as mussel foot proteins Mfps.[23-25]

Up to date, six Mfps, Mfp-1 through Mfp-6, have been identified from the adhesive plaques in several species of mussel, such as $M.$ $galloprovincialis,$ $M.$ $californianus$, etc. Mfp1, Mfp3 and Mfp 5 are not the most abundant proteins, but contain the largest amount of the catechol-containing amino acid 3,4-dihydroxy-L-phenylalanine (L-Dopa), with about 15 mol %, 20 mol % and 30 mol %, within their respective sequence.[26] One of the Mfps' unique features is the high percentage of the L-Dopa content positioned in the vicinity of a lysine amino acid (Lys), in their protein sequence.[24] Both L-Dopa and Lys are crucial for Mfps adhesion. It was demonstrated that underwater adhesion is due to a synergy between a certain amount of both catechol and guanidinium side chains when both are part of the same molecule.[27] More recently, it is also demonstrated that flanking Lys enhanced the surface adhesion of Dopa and plays important roles in underwater mussel adhesion.[28] Additionally, the ability of the catechol moieties to interact with other amino acids and even metals in the form of both metal ions and oxides render them appealing as tissue adhesives.[29]

Wet adhesion aided by Dopa peptide has been largely exploited, where adhesion is achieved by absorption on surfaces, crosslinking, and coacervates formation.[30-34] The insertion of catechol moieties with or without flanking lysine has been recently used in several applications to increase the wet adhesive properties of polypeptides. Adhesive hydrogels containing catechol moieties based on chitosan[35], hyaluronic acid[36-37], PEG[38], ε-poly-lysine[39] were developed often wise with the scope to intervene in the medical field[40-41] or marine engineering applications[42]. Activation of these adhesives can be achieved by several means such as pH[31], temperature change[35] and even pressure[43]. All these studies demonstrate the enhancement of adhesive properties of polymers in the presence of Dopa. Moreover, it has also been demonstrated, by using Atomic Force Microscopy (AFM), how the conjoint presence of Lys and Dopa in the Mfps protein provides better adhesion to $TiO_2$ substrates.[44] The advantage of using Force spectroscopy based measurement in AFM setup is the capability of working in liquid and characterizing not only the topography but also mechanical and adhesive properties of soft materials, including hydrogels and cells.[11,46]

Wet adhesion is demanded in various applications and yet is challenging to be achieved. As described above, underwater adhesion is realized by a delicate balance of supramolecular/surface architectures, polyelectrolyte complex, and catechol chemistry in nature. Underwater adhesive proteins secreted by e.g. mussels and barnacles in order to adhere to surfaces in wet condition have high content of the unusual cathecolic amino acid L-Dopa and of lysine amino acid.

Due to the limited available wet adhesion materials, there exists a need for a new class of adhesive peptides. The exploration of including L-Dopa in such wet adhesion materials would be promising.

SUMMARY

It is therefore desirable to provide a wet adhesion compound that is capable of forming a hydrogel that meets at least some of the above requirements to a higher extent than currently available hydrogels and that is not restricted by the above mentioned limitations.

According to a first broad aspect of the present disclosure, an ultrashort peptide sequences having a general formula:

wherein the total number of amino acids of the ultrashort peptide is 4-12 amino acids; wherein A is comprised of a polar amino acid, selected from the group consisting of: levodopa, derivatives of levodepa, aspartic acid, glutamic acid, asparagine, glutamine, lysine, 5-N-ethyl-glutamine (theanine), citrulline, thio-citrulline, cysteine, homocysteine, methionine, ethionine, selenomethionine, telluromethionine, threonine, allothreonine, serine, homoserine, tyrosine, histidine, arginine, homoarginine, ornithine, lysine, N(6)-carboxymethyllysine, histidine, 2,4-diaminobutyric acid (Dab), 2,3-diaminopropionic acid (Dap), and N(6)-carboxymethyllysine, with n being an integer selected from 0-1 and p being an integer selected from 1-6, preferably 1-2, wherein B is comprised of a hydrophobic amino acid selected from the group consisting of: isoleucine, norleucine, leucine, valine, alanine, glycine, homoallylglycine, homopropargylglycine, phenylalanine, tyrosine, tryptophan, methionine, proline, and cyclohexylalanine, with m being an integer selected from 3-6; wherein n+p=1-6, and wherein at least one amino acid of A is levodopa or its derivative, wherein the derivatives of levodepa is selected from the group consisting of 3,4,5-trihydroxyphenylalanine, 3,4,6-trihydroxyphenylalanine, β,3-Dihydroxytyrosine.

According to a second broad aspect of the present disclosure, a hydrogel comprising the peptides is provided according to the present disclosure.

According to a third broad aspect of the present disclosure, a method of preparing a hydrogel, the method comprising dissolving a peptide is provided in an aqueous solution or buffer solution or an organic solution, respectively.

Other aspects and features of the present disclosure will become apparent to those skilled in the art upon review of the following description of specific embodiments of the invention in conjunction with the accompanying figures.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

IIZKDo according to an embodiment of the present disclosure.

Figure 14:
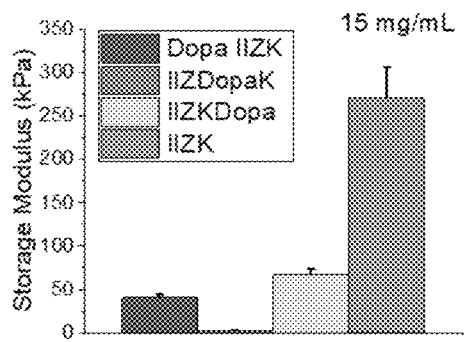

FIG. 14 is a graph showing the storage modulus of DoIIZK, IIZDoK and IIZKDo compared to IIZK according to an embodiment of the present disclosure.

Figure 15:
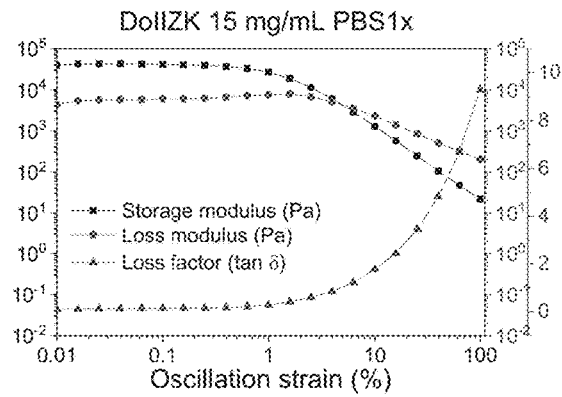

FIG. 15 is a graph showing the rheology measurements of hydrogel of DoIIZK in response to oscillation strain according to an embodiment of the present disclosure.

Figure 16:
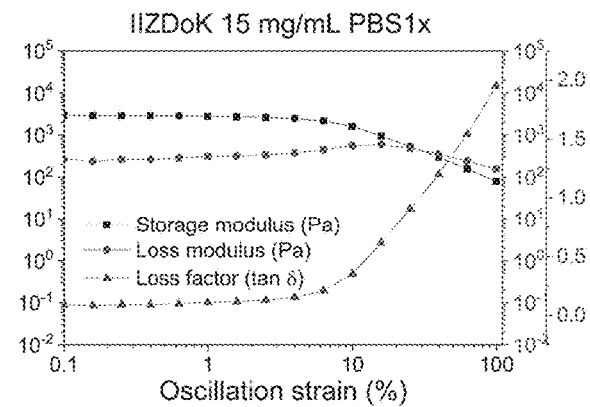

FIG. 16 is a graph showing the rheology measurements of hydrogel of IIZDoK in response to oscillation strain according to an embodiment of the present disclosure.

Figure 17:
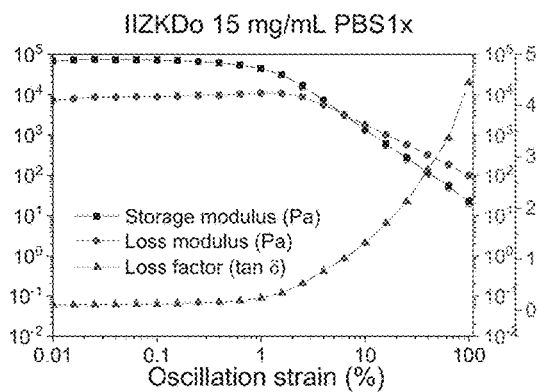

FIG. 17 is a graph showing the rheology measurements of hydrogel of IIZKDo in response to oscillation strain according to an embodiment of the present disclosure.

Figure 18:
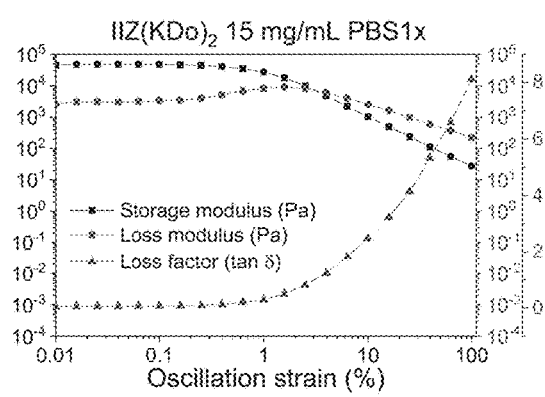

FIG. 18 is a graph showing the rheology measurements of hydrogel of $IIZ(KDo)_2$ in response to oscillation strain according to an embodiment of the present disclosure.

Figure 19:
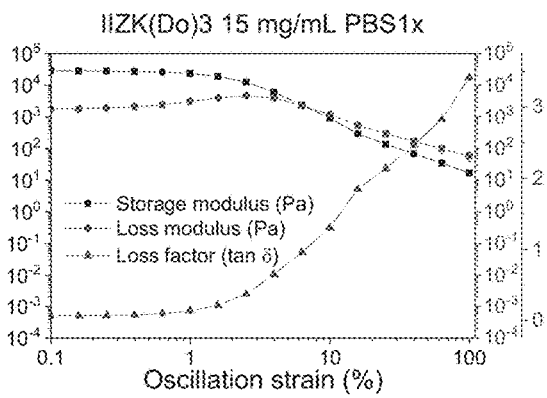

FIG. 19 is a graph showing the rheology measurements of hydrogel of $IIZ(KDo)_3$ in response to oscillation strain according to an embodiment of the present disclosure.

Figure 20:
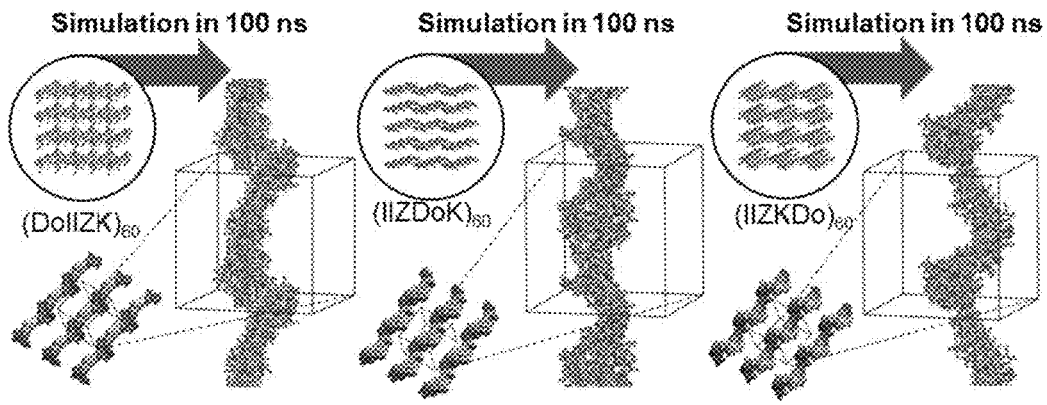

FIG. 20 is a graph showing the fibril structure for 60 peptides assembles at 100 ns of MD simulation according to an embodiment of the present disclosure.

Figure 21:
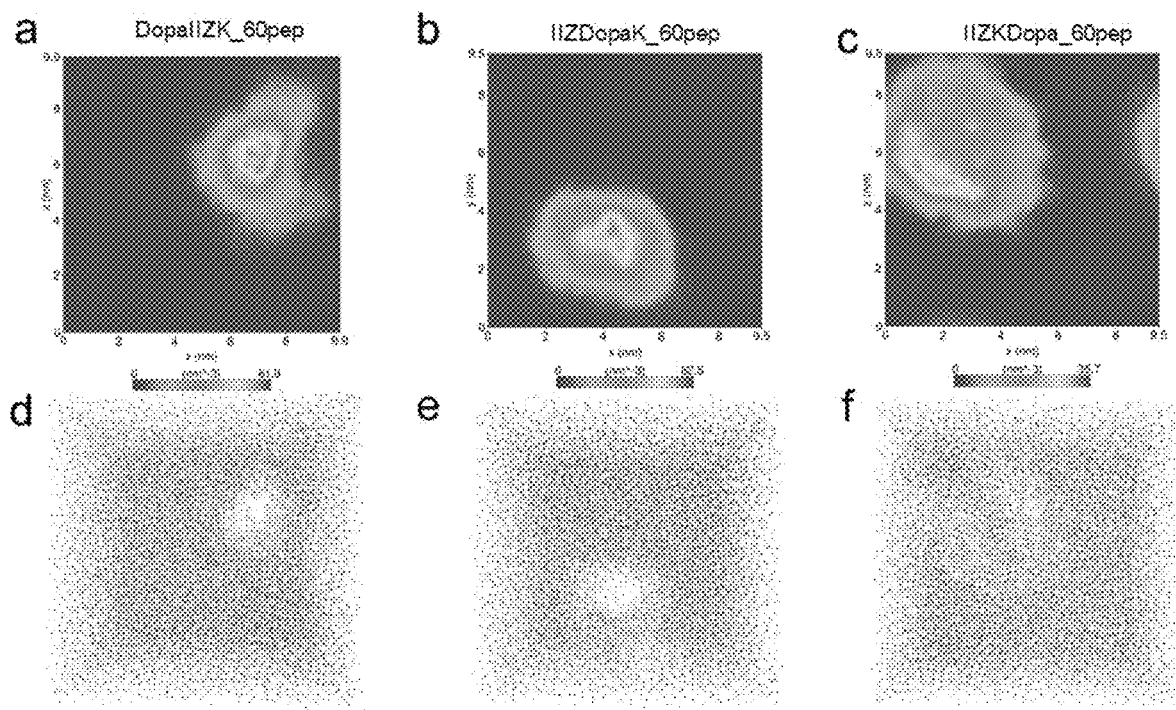

FIG. 21 is a graph showing the density maps and water distribution of DoIIZK, IIZDoK and IZZKDo according to an embodiment of the present disclosure.

Figure 22:
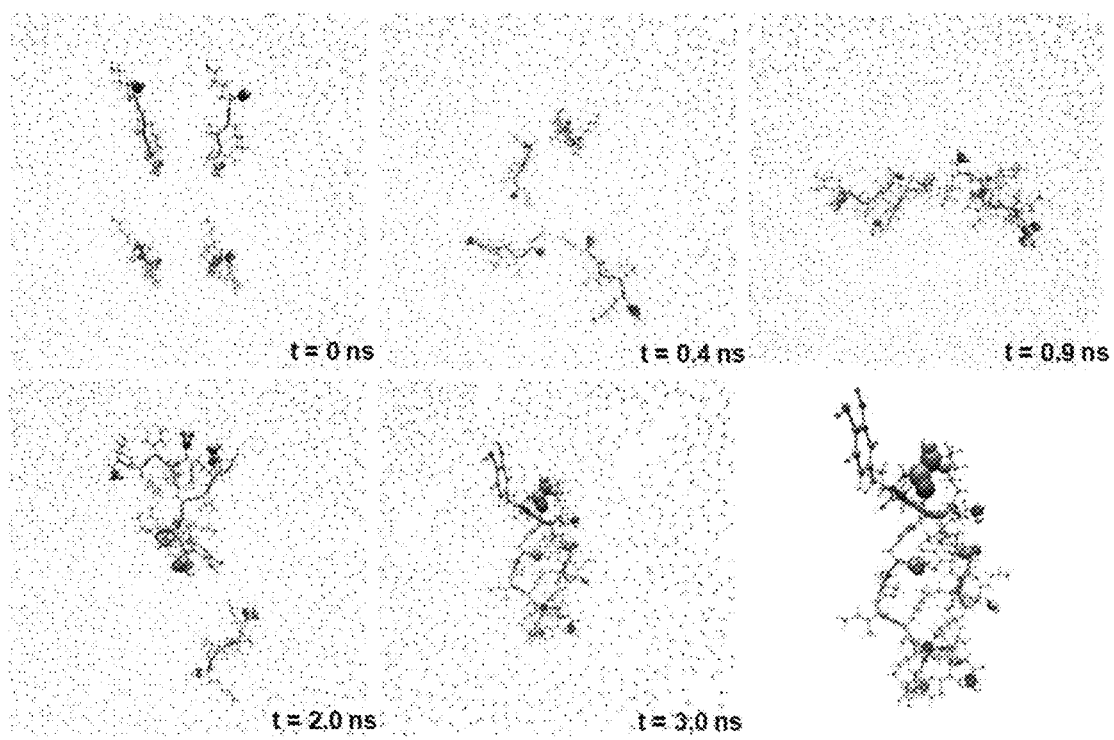

FIG. 22 is a graph showing the snapshots from the simulation of four DoIIZK peptides according to an embodiment of the present disclosure.

Figure 23:
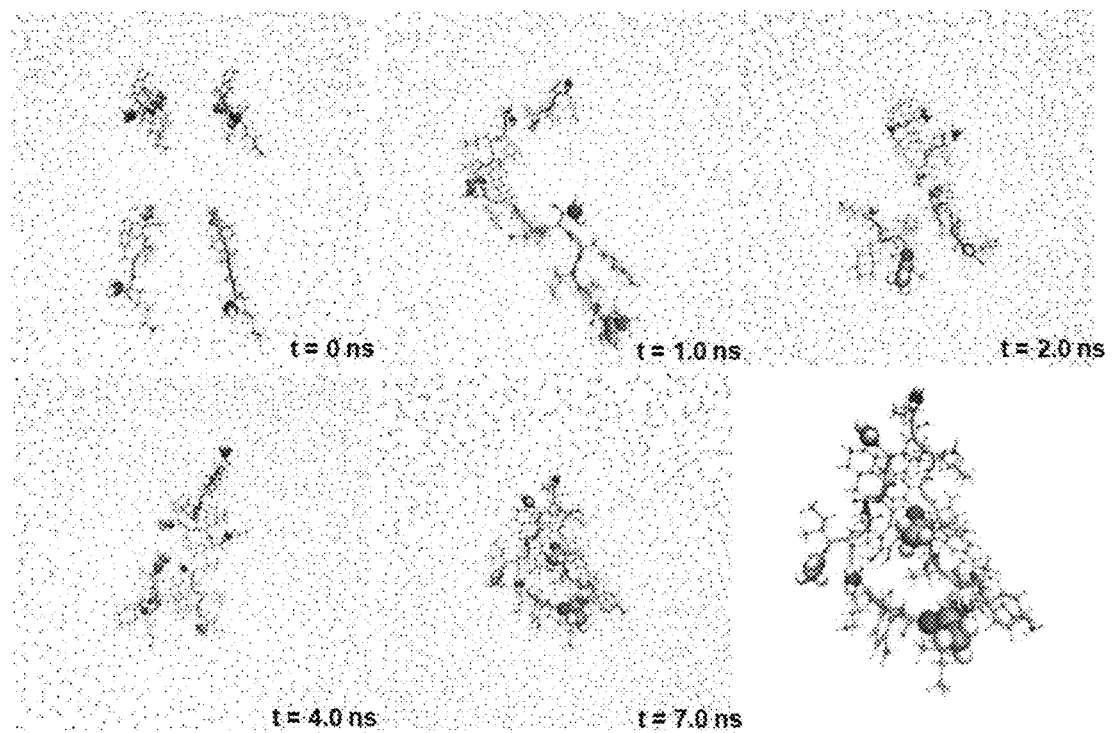

FIG. 23 is a graph showing the snapshots from the simulation of four IIZDoK peptides according to an embodiment of the present disclosure.

Figure 24:
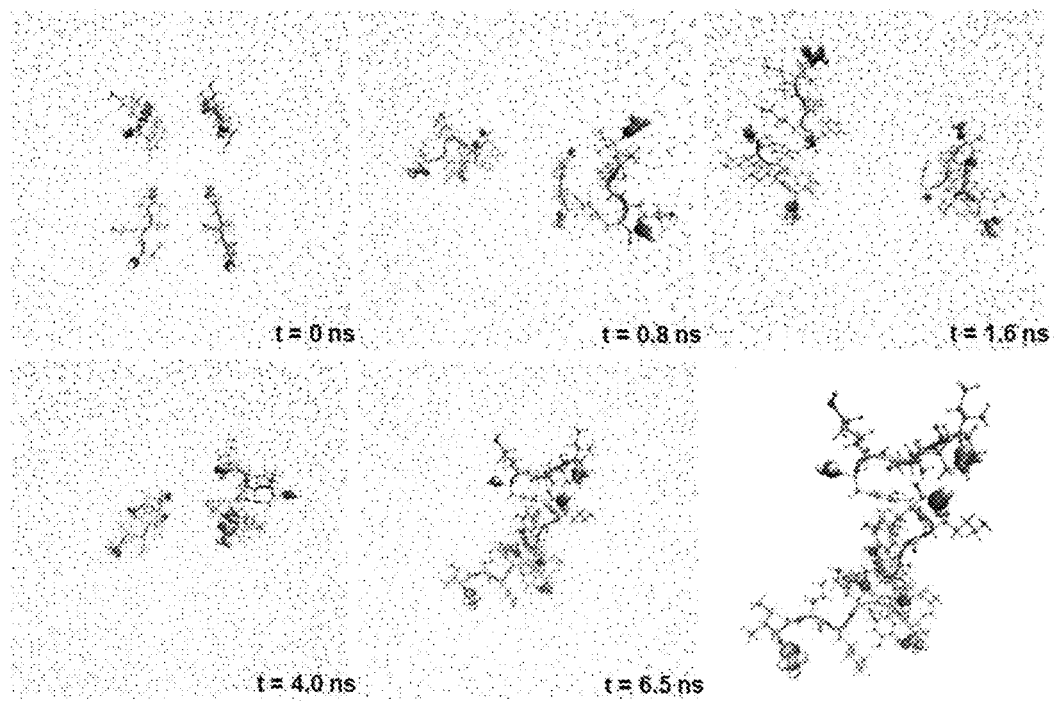

FIG. 24 is a graph showing the snapshots from the simulation of four IIZKDo peptides according to an embodiment of the present disclosure.

Figure 25:
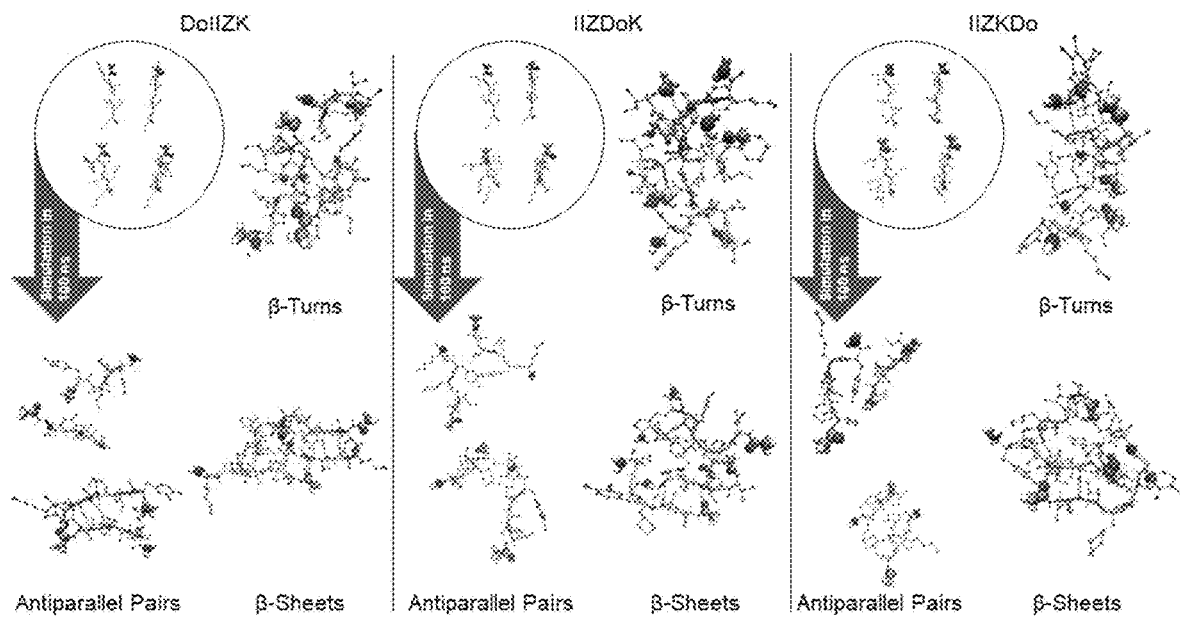

FIG. 25 is a graph showing the secondary structures formed by peptides during simulation according to an embodiment of the present disclosure.

Figure 26:
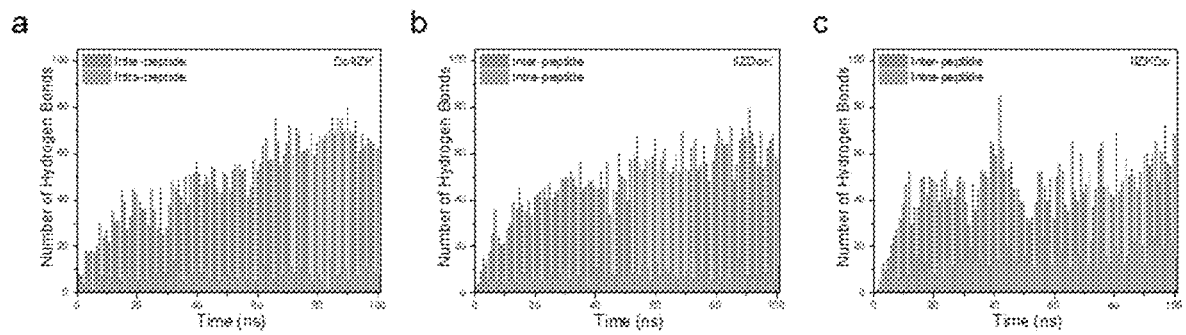

FIG. 26 is a graph showing the hydrogen bonds analysis during the 100 ns simulation of 60-DoIIZK/IIZDoK/IIZKDo peptides assembly according to an embodiment of the present disclosure.

Figure 27:
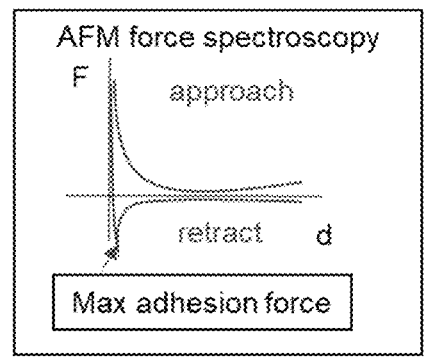

FIG. 27 is a graph showing a typical force-distance AFM curve to identify maximum adhesion force according to an embodiment of the present disclosure.

Figure 28:
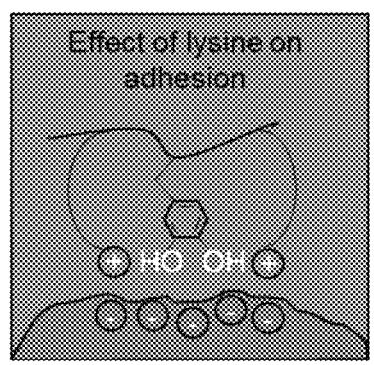

FIG. 28 is a graph showing the effect of lysine on adhesion to negatively charged surfaces according to an embodiment of the present disclosure.

Figure 29:
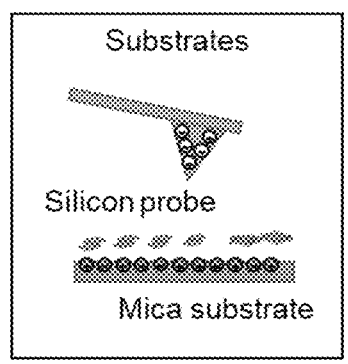

FIG. 29 is a graph showing the setup of probe and substrate in AFM measurement according to an embodiment of the present disclosure.

Figure 30:
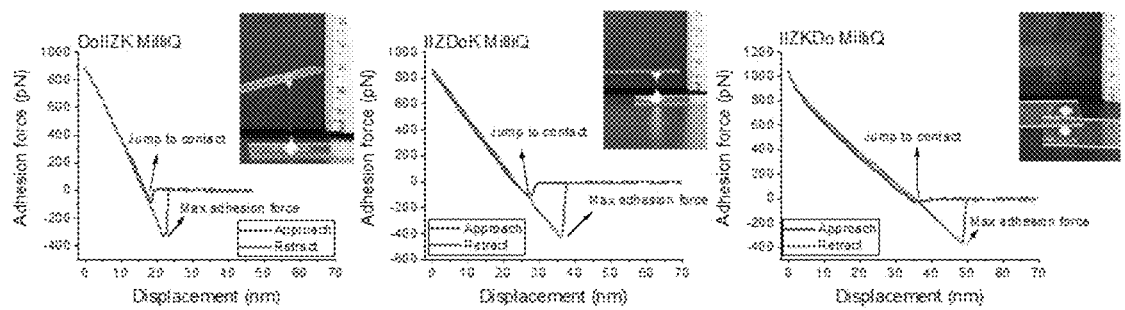

FIG. 30 is a graph showing the AFM curves for DoIIZK, IIZKDo, and IIZDoK in MilliQ® water according to an embodiment of the present disclosure.

Figure 31:
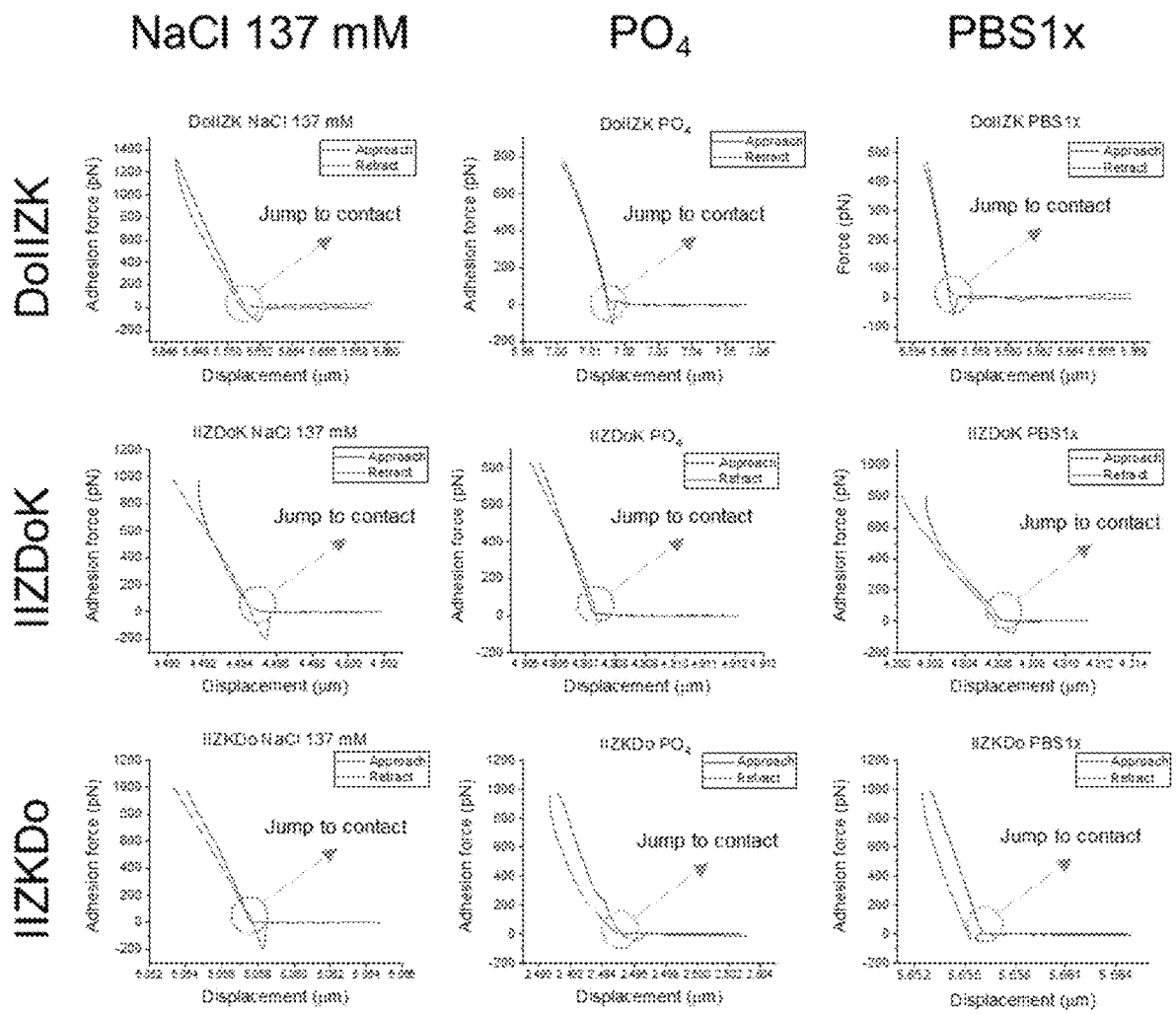

FIG. 31 is a graph showing the AFM curves for DoIIZK, IIZKDo, and IIZDoK in different buffers according to an embodiment of the present disclosure.

Figure 32:
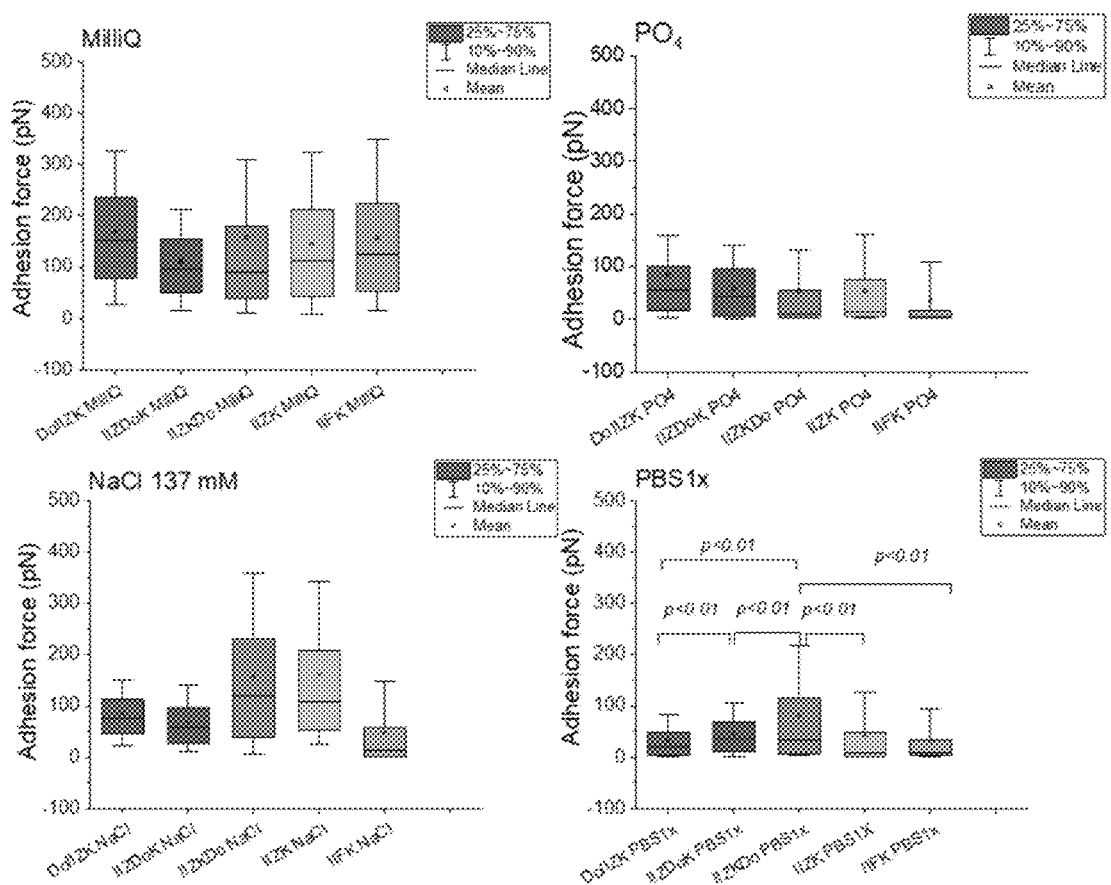

FIG. 32 is a box plot graph showing the AFM results of maximum force of adhesion populations according to an embodiment of the present disclosure.

Figure 33:
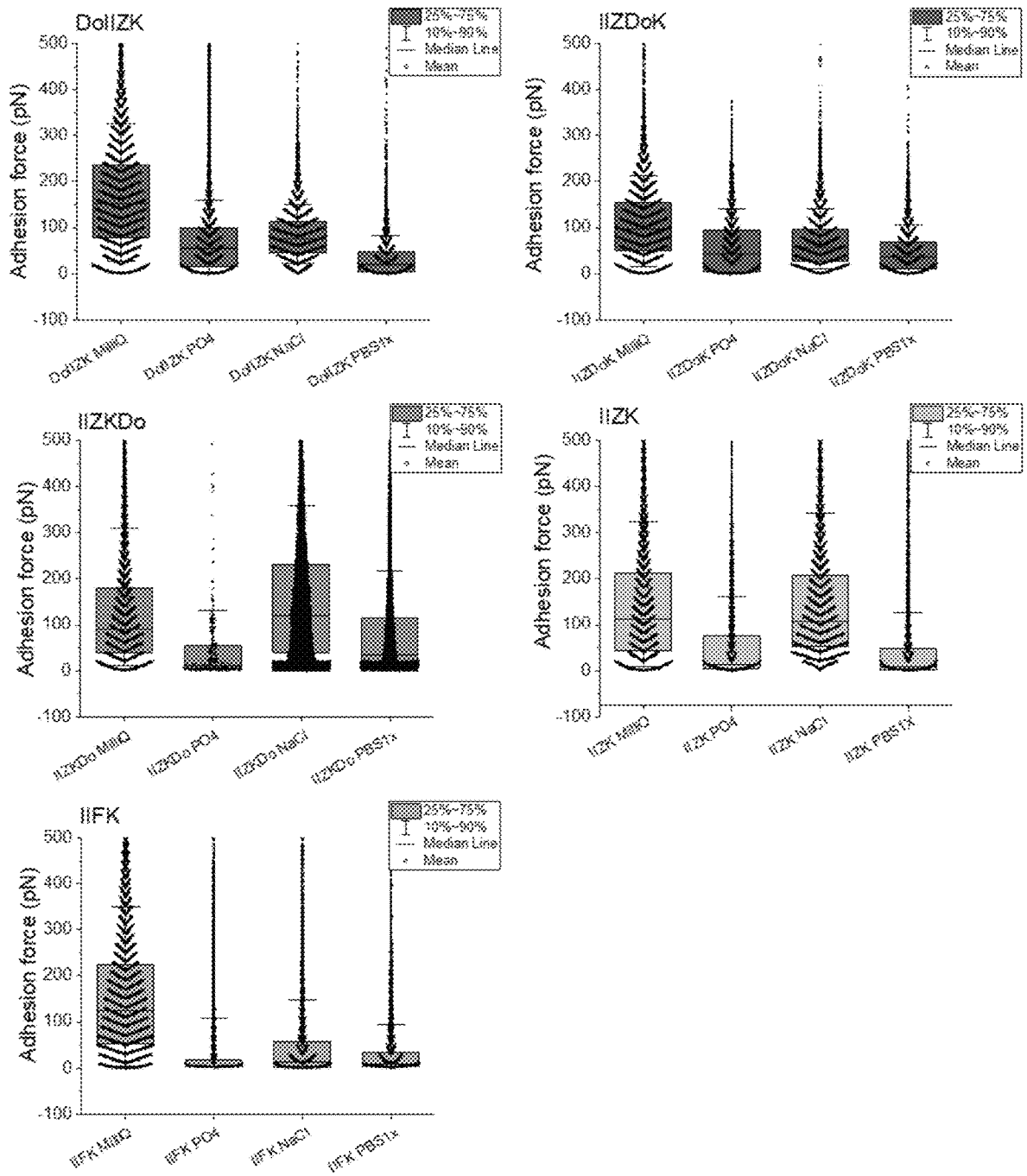

FIG. 33 is a box plot graph showing the AFM force spectroscopy on DoIIZK, IIZDoK, IIZKDo, IIFK, and IIZK in different solvents according to an embodiment of the present disclosure.

Figure 34:
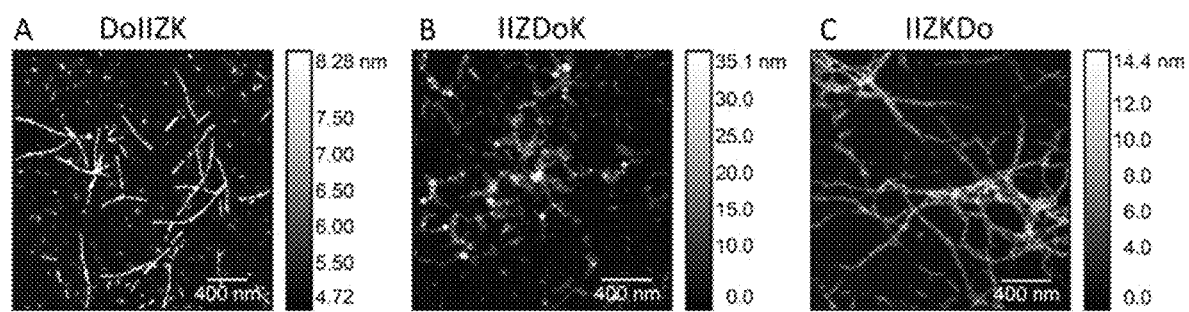

FIG. 34 is a photo showing the AFM topography in air after force spectroscopy measurement in liquid according to an embodiment of the present disclosure.

Figure 35:
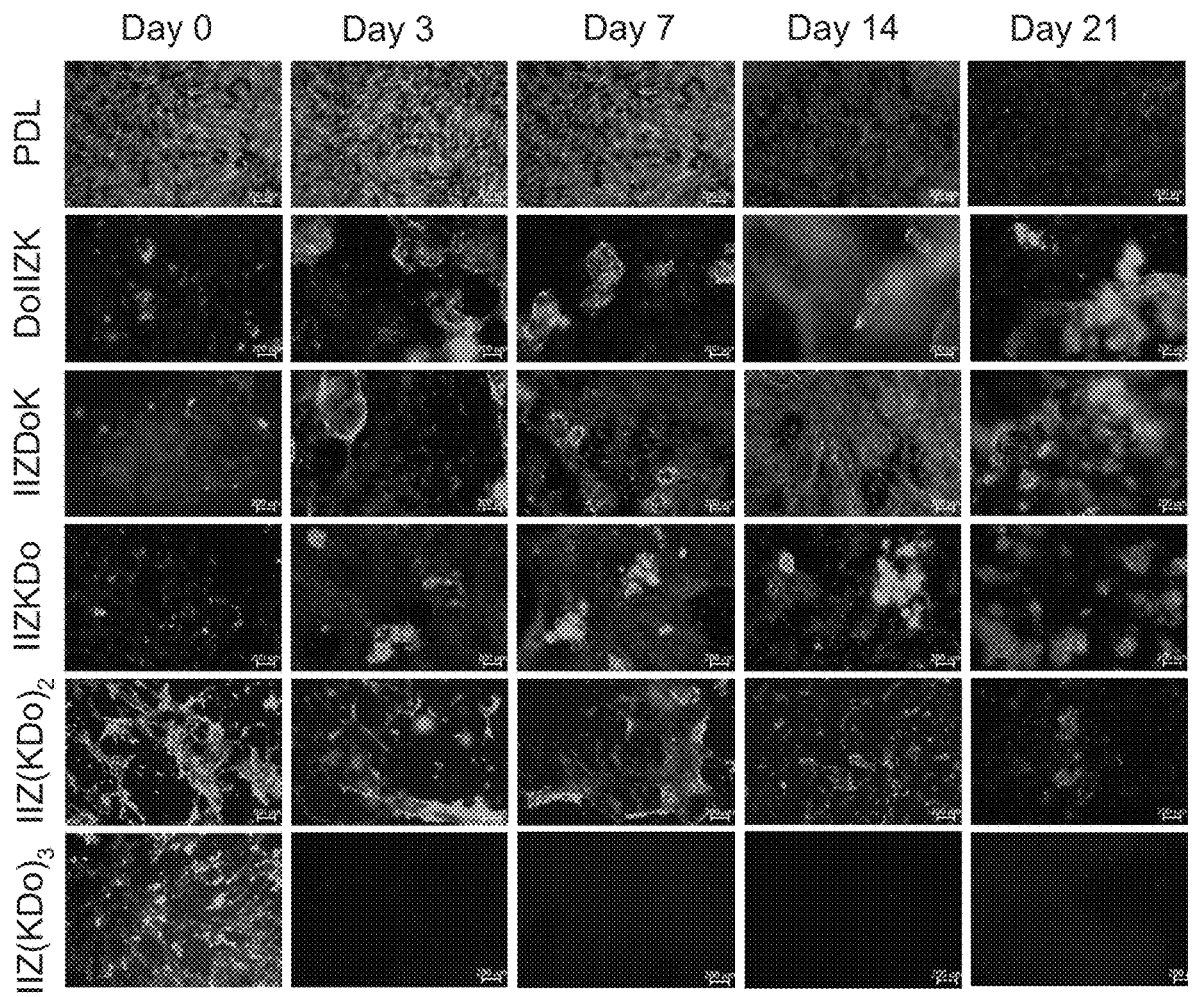

FIG. 35 is a photo showing the cytotoxicity of DoIIZK, IIZDoK, IIZKDo, IIZ(KDo)$_2$ and IIZ(KDo)$_3$ to C2C12 cells encapsulated in peptide hydrogels according to an embodiment of the present disclosure.

Figure 36:
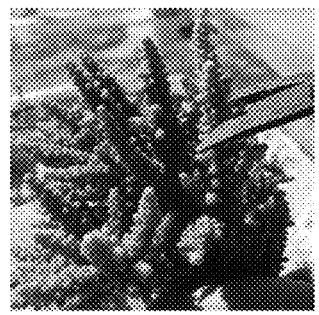

FIG. 36 is a photo showing *Acropora hemprichii* fragment being cut from a coral according to an embodiment of the present disclosure.

Figure 37:
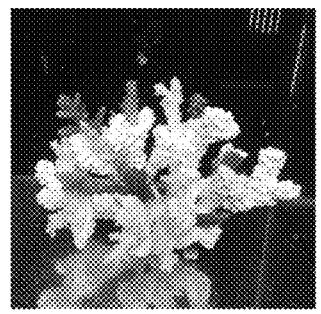

FIG. 37 is a photo showing several fragments of *Acropora* spp. glued on a 3D printed scaffold by using IIZKDo peptide according to an embodiment of the present disclosure.

Figure 38:

FIG. 38 is a photo showing the entire coral piece 19 days after fragments of *Acropora* spp. are glued and cultured in aquarium with sea water according to an embodiment of the present disclosure.

Figure 39:
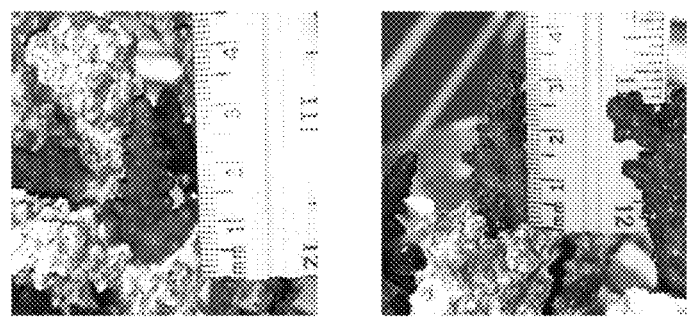

FIG. 39 is a photo showing details of two glued fragments with healthy status according to an embodiment of the present disclosure.

Figure 40:
Figure 40:
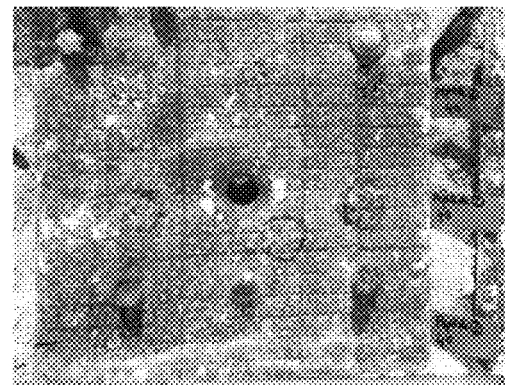

FIG. 40 is a photo showing coral adhesion to tile using DoIIZK, IIZDoK and IIZKDo in sea water tank according to an embodiment of the present disclosure.

Figure 41:
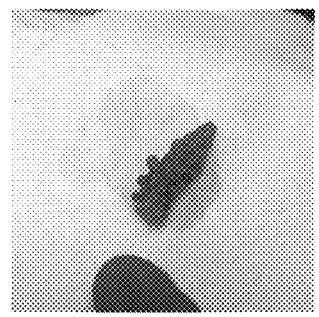

FIG. 41 is a photo showing a coral piece cut from the donor coral according to an embodiment of the present disclosure.

Figure 42:
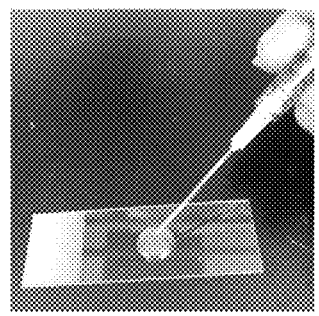
Figure 42:
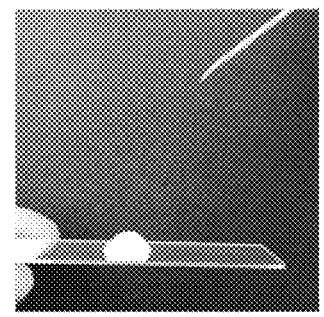

FIG. 42 is a photo showing the preparation of the IIZKDo glue according to an embodiment of the present disclosure.

Figure 43:
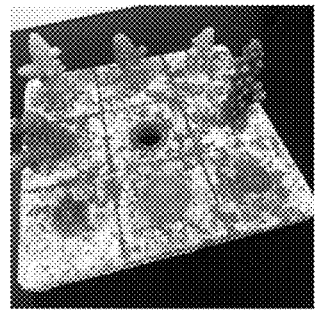

FIG. 43 is a photo showing the tile in water with glued coral fragments after 3 days of culturing according to an embodiment of the present disclosure.

Figure 44:
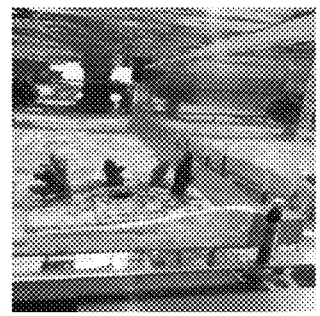

FIG. 44 is a photo showing the tile in the sea water tank according to an embodiment of the present disclosure.

Figure 45:
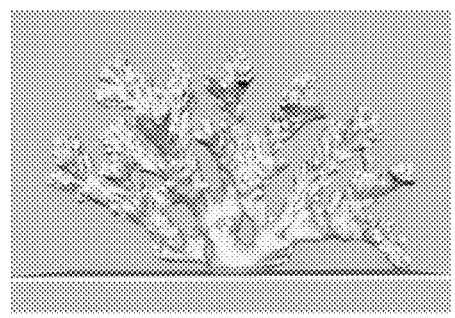

FIG. 45 is a photo showing the 3D printed coral skeleton according to an embodiment of the present disclosure.

DETAILED DESCRIPTION OF THE INVENTION

Definitions

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present disclosure, the term "comprising", the term "having", the term "including," and variations of these words are intended to be open-ended and mean that there may be additional elements other than the listed elements.

For purposes of the present disclosure, directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing figures may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present disclosure, the term "gel", and "nanogel" are used interchangeably. These terms gel and nanogel refer to a network of polymer chains, entrapping water or other aqueous solutions, such as physiological buffers or organic solvents. In an embodiment of the present disclosure, the polymer chains may be a peptide with repetitive sequences.

For purposes of the present disclosure, the term "hydrogel" refers to the gel material formed by the self-assembly of the ultrashort peptides occurs in aqueous solution.

For purposes of the present disclosure, the term "organogel" refers to the gel material formed by the self-assembly of the ultrashort peptides occurs in organic solvents.

For purposes of the present disclosure, the term "ultrashort peptide" refers to a sequence containing 3-7 amino acids. The peptides according an aspect of the present disclosure are also particularly useful for formulating aqueous or other solvent compositions, which may be used as building block of 3D structures.

For purposes of the present disclosure, the term "scaffolds" as used herein means the supramolecular network structures made from self-assembling ultra-short peptide or other polymer materials in the bioinks that provide support for the cellular components.

For purposes of the present disclosure, the term "pentapeptides" refers to peptides made of five amino acids.

For purposes of the present disclosure, the terms "Dopa", "L-Dopa" and "Do" when used in peptide sequence are used interchangeably. These terms refer to levodopa, which is also known as 3,4-dihydroxy-L-phenylalanine.

For purposes of the present disclosure, the term "biocompatible", which also can be referred to as "tissue compatible", as used herein, refers to the property of a gel that produces little if any adverse biological response when used in vitro or in vivo.

For purposes of the present disclosure, the term "PBS" refers to a buffer solution commonly used in biological research, which is an abbreviation of phosphate-buffered saline. It is a water-based salt solution, helping to maintain a constant pH, as well as osmolarity and ion concentrations to match those of most cells. In some embodiments, PBS may include a water-based salt solution containing disodium hydrogen phosphate, sodium chloride and, in some formulations, potassium chloride and potassium dihydrogen phosphate.

For purposes of the present disclosure, the term "Wang resin" refers to a standard support for batch synthesis of peptide, which includes 4-Benzyloxybenzyl alcohol resin.

For purposes of the present disclosure, the term "FBS" refers to fetal bovine serum, which comes from the blood drawn from a bovine fetus via a closed system of collection, and is commonly used in cell culture protocols.

For purposes of the present disclosure, the terms "v/v" and "% v/v" are used interchangeably. These terms refer to Volume concentration of a solution.

For purposes of the present disclosure, the term "P/S" refers to penicillin-streptomycin solution.

For purposes of the present disclosure, the term "amphiphilic" and "amphiphilicity" refer to being a compound consisting of molecules having a water-soluble group at one end and a water-insoluble group at the other end.

For purposes of the present disclosure, the term "hydrophobic" and "hydrophobicity" refer to the property of a molecule tending to repel or fail to mix with water.

For purposes of the present disclosure, the term "critical gelation concentration" or "CGC" refers to the concentration of peptide when the soft solid gel is formed.

For purposes of the present disclosure, the term "printability" and "bioprintability" refer to the suitability of peptide for 3D printing. In particular, it refers to the suitable speed of self-assembly at certain concentration, and viscosity. The speed of forming gel and viscosity need to be high enough so that a structure with certain height can be printed without collapsing. On the other hand, the speed and viscosity need to be low enough so that the peptide will not clog the nozzle of bioprinters.

For purposes of the present disclosure, the term "mol %" refers to percentage of molecules. With regard to the peptide sequences in the present disclosure, the term "mol %" refers to the ratio number of molecules of a particular amino acid to the total number of amino acid molecules in the peptide sequence. For instance, the sequence DoIIZK contains one molecule of Dopa and a total of five amino acids. Thus, the mol % of Dopa is 1/5, which equals to 20%.

Description

In one embodiment, the physico-chemical and adhesive properties of SAP peptides containing lysine are impacted by the catechol moiety positioning in the SAP sequence.

In one embodiment, the position of Dopa affects the capability of the SAP to form extracellular matrix (ECM) resembling fibres, the ability to form hydrogels, and their mechanical properties.

In one embodiment, the vicinity of the catechol moiety to the lysine residue influences the adhesive properties of the self-assembled peptide. The mechanism of such influences is determined by the use of AFM force spectroscopy in liquid.

In one embodiment, the presence of ionic species in solution affects only slightly the adhesive properties of the hydrogel containing catechol moiety in the C-terminus position of the peptide sequence.

In one embodiment, the adhesive properties of catechol modified SAP makes the SAP suitable wet adhesives in marine environment for reef coral restoration.

Characterization of Peptide Assemblies Containing Catechol

In one embodiment, the peptide in the present disclosure are Dopa-peptides, including:

Peptide 1a: DopaIIZK
Peptide 2a: IIZDopaK
Peptide 3a: IIZKDopa
Peptide 3b: IIZ(KDopa)$_2$
Peptide 3c: IIZ(KDopa)$_3$ Wherein Dopa is levodopa, I is isoleucine, K is lysine, and Z is cyclohexylalanine.

Figure 1:
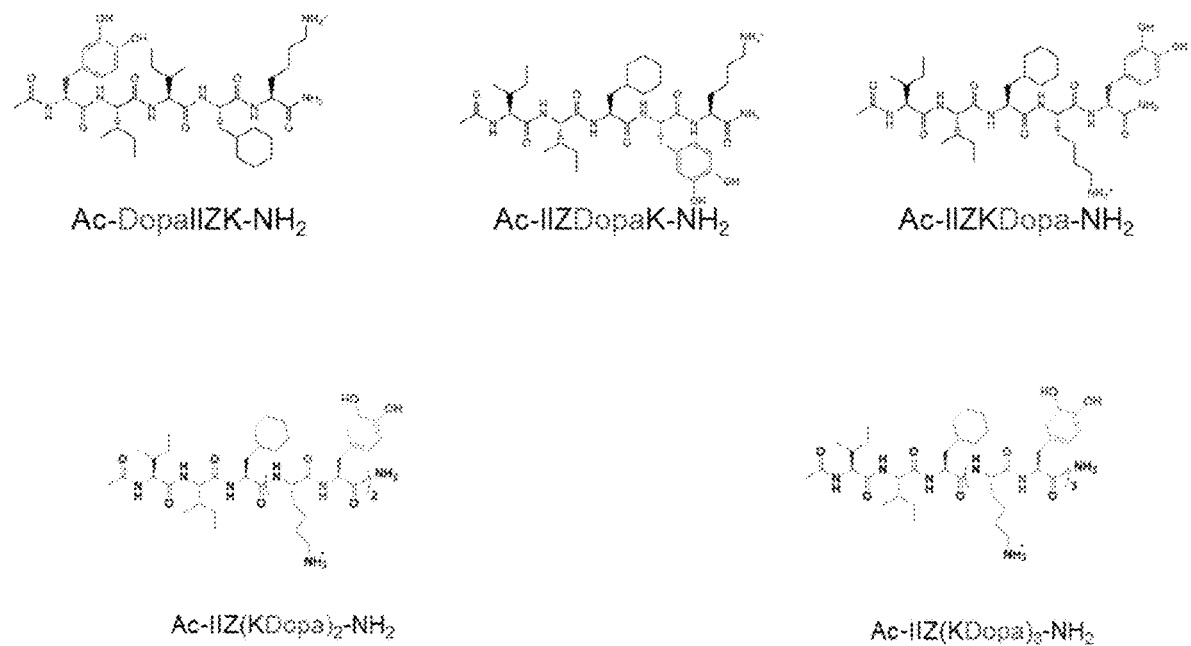
FIG. 1 is a graph showing the chemical structures of the synthesized Dopa-peptides according to an embodiment of the present disclosure.

FIG. 1 illustrates the chemical structures of the above Dopa-peptides.

The $^1$H NMR results of DopaIIZK, IIZDopaK and IIZKDopa are summarized below:

DoIIZK Peptide:
$^1$H NMR (500 MHz, DMSO-d$_6$) δ 8.01 (s, 2H), 7.92 (s, 1H), 7.85 (m, 1H), 7.73 (d, 1H), 7.28 (d, 1H), 7.04 (d, 1H), 6.65-6.62 (m, 1H), 6.59-6.56 (m, 1H), 4.43 (t, 1H), 4.30 (d, 2H), 4.20-4.11 (m, 2H), 2.80-2.71 (m, 2H), 1.74 (s, 3H), 1.66-1.59 (m, 4H), 1.51-1.44 (m, 5H), 1.29-1.25 (m, 2H), 1.11-1.07 (m, 3H), 0.83-0.78 (t, 13H).

IIZDoK Peptide:
$^1$H NMR (500 MHz, DMSO-d$_6$) δ 7.93 (t, 3H), 7.83 (q, 2H), 7.85 (d, 1H), 7.69 (d, 1H), 7.09 (s, 1H), 7.03 (s, 1H), 6.61-6.55 (m, 2H), 6.44 (d, 1H), 4.36 (d, 1H), 4.26 (d, 1H), 4.20-4.15 (m, 1H), 4.13-4.08 (m, 2H), 2.73 (t, 2H), 2.63 (d, 1H), 1.85 (s, 3H), 1.70-1.54 (m, 7H), 1.51-1.43 (m, 2H), 1.41-1.30 (m, 3H), 1.29-1.21 (m, 3H), 1.11-1.02 (m, 4H), 0.83-0.73 (t, 13H).

IIZKDo Peptide:
$^1$H NMR (500 MHz, DMSO-d$_6$) δ 7.94 (d, 2H), 7.89 (d, 1H), 7.85 (d, 1H), 7.67 (d, 1H), 7.32 (s, 1H), 7.04 (s, 1H), 6.61 (d, 2H), 6.44 (d, 1H), 4.35-4.27 (m, 2H), 4.17 (q, 3H), 2.81 (q, 1H), 2.73 (t, 2H), 2.65 (d, J=7.7 Hz, 1H), 1.87 (s, 3H), 1.51-1.40 (m, 7H), 1.30-1.21 (m, 3H), 1.10 (t, 4H), 0.82 (t, 13H).

In one embodiment, SAP peptides have the ability to self-assemble into nanofibrous hydrogels due to their amphiphilic nature.

In one embodiment, the hydrophilic part of thee the amphiphilic self-assembling peptides can be made of different polar amino acids.

The incorporation of serine, aspartic acid and glutamic acid have been consistently generate fast gelating hydrogels. However. These amino acids make the solution very acidic, compromising its biocompatibility for cell culture. In one embodiment, lysine was introduced as the hydrophilic amino acid to reduce the acidity of the solution, while still providing the positive charge necessary to the self-assembly[47].

IIZ sequence plays an important role to preserve hydrophobicity in the peptide sequence. In one embodiment, Dopa-peptides have been synthesized by incorporating the Dopa at some strategic positions such as before and after IIZ followed by a lysine residue, giving the peptide its hydrophobicity. The choice on the IIZK tetrapeptide is because IIZK shows good biocompatibility and bioprintability.[11]

In another embodiment, Dopa was incorporated at the C-terminus of the IIZ sequence but at N-terminus of lysine, leaving lysine at the C-terminus of the peptide.

In one embodiment, the addition of the catechol moiety at different positions along the SAP peptide influenced the gelation properties of the polymers.

In one embodiment, peptide DopaIIZK has a critical gelation concentration (CGC) of 2 mg/mL in phosphate-buffered saline (1×PBS), while peptide IIZDopaK was found to gel at 4 mg/mL and peptide IIZKDopa at 3 mg/mL.

Figure 2:
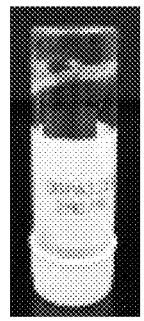
FIG. 2 is a photo showing the hydrogels formed by different Dopa-peptides according to an embodiment of the present disclosure.
Figure 2:
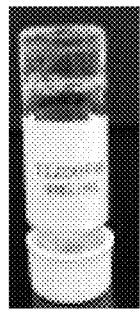
Figure 2:
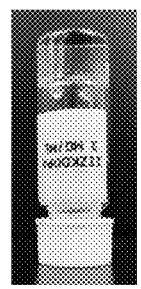
Figure 2:
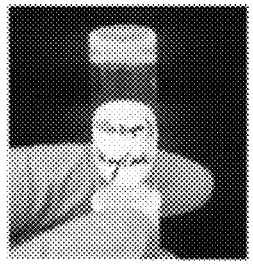
Figure 2:
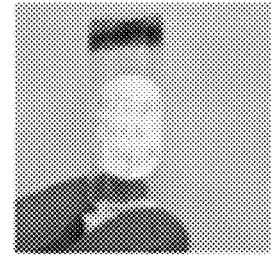

In another embodiment, all five Dopa-peptides form hydrogels, as shown in FIG. 2. The hydrogels formed at the bottom of the vials, which is at the top of each photos showing the results of vial inversion test in FIG. 2.

Figure 3:
FIG. 3 is a photo showing the hydrogels formed by peptides DopaIIZK, IIZDopaK and IIZKDopa at different concentration according to an embodiment of the present disclosure.
Figure 3:
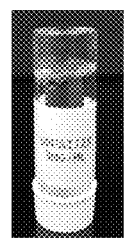
Figure 3:
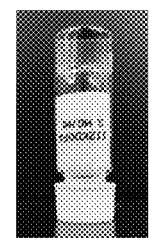
Figure 3:
Figure 3:
Figure 3:
Figure 3:
Figure 3:
Figure 3:

In another embodiment, it takes different amount of time for peptides DopaIIZK, IIZDopaK and IIZKDopa to form gels at different concentrations. The gels formed by peptides DopaIIZK, IIZDopaK and IIZKDopa at different concentrations are shown in FIG. 3.

The critical gelation concentration (CGC) and gelation time of hydrogels formed by the catechol peptides in 1×PBS determined by vial inversion test are summarized below:

|  | DopaIIZK | IIZDopaK | IIZKDopa |
| --- | --- | --- | --- |
| 1 mg/mL | Not gelating | Not gelating | Not gelating |
| 2 mg/mL | >45 min | Not gelating | Not gelating |
| 3 mg/mL | >30 min | Not gelating | >30 min |
| 4 mg/mL | >20 min | >80 min | >21 min |
| 5 mg/mL | >10 min | >75 min | >16 min |

In one embodiment, peptide with Dopa at the N-terminus of the peptide had a shorter gelation time at lower concentration, due to the position of Dopa at the N-terminus of hydrophobic groups, including isoleucine (I) and cyclohexylalanine (Z), followed by a polar group, lysine (K) at the C-terminus of Z.

In one embodiment, the gelation efficiency proceeds as follows: DoIIZK (CG at 2 mg/mL; gelation at 45 minutes) >IIZKDo (CGC at 3 mg/mL; gelation at 30 minutes) >IIZDoK (CGC at 4 mg/mL; gelation at 80 minutes).

In one embodiment, the faster gelating peptide is DoIIZK, due to the hydrophobicity of Dopa. In one embodiment, the gelation times and concentration are dramatically changed in the IIZDoK peptide, indicating that catechol moiety in this position is in fact disrupting the self-assembly process.

These observations suggest that self-assembly and hydrogelation is impacted by the ratio and position of the hydrophilic and hydrophobic elements in the peptide motif. Furthermore, the position of the Dopa within the peptide plays a key role for hydrogelation in terms of both time and concentration.

The Structure of the Dopa-Peptide Hydrogels

Figure 4:
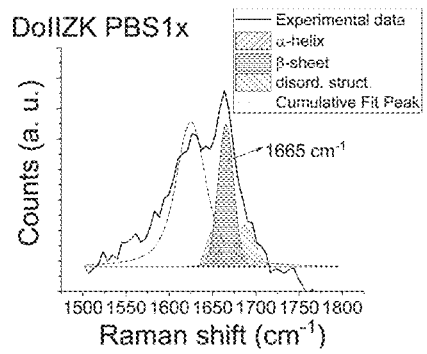
FIG. 4 is a graph showing the Raman spectroscopy of DoIIZK at 5 mg/mL according to an embodiment of the present disclosure.
Figure 5:
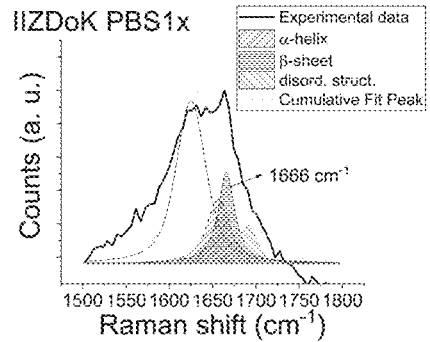
FIG. 5 is a graph showing the Raman spectroscopy of IIZDoK at 5 mg/mL according to an embodiment of the present disclosure.
Figure 6:
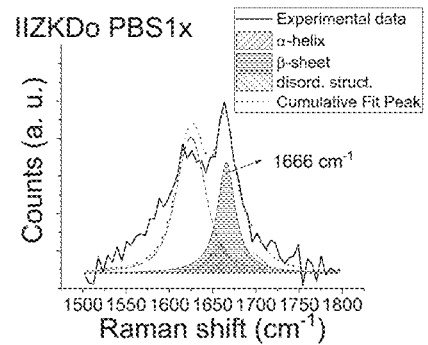
FIG. 6 is a graph showing the Raman spectroscopy of IIZKDo at 5 mg/mL according to an embodiment of the present disclosure.

In one embodiment, the secondary structure of the IIZDoK peptide contains a larger amount of α-helix structure than DoIIZK and IIZKDo peptides that preferentially contain β-turn, as can be appreciated in the Raman spectroscopy signatures of the three peptides. The Raman spectroscopy signatures of the three peptides are shown in FIGS. 4-6. The Raman peaks and integrated areas under the related peaks for each peptide in 1×PBS at 5 mg/mL are summarized in the Table below:

|  | α-helix Raman shift (cm$^{-1}$); Area % | β-turn Raman shift (cm$^{-1}$); Area % | Disordered structure Raman shift (cm$^{-1}$); Area % |
| --- | --- | --- | --- |
| DoIIZK | 1650; 13% | 1665; 65% | 1687; 22% |
| IIZDoK | 1656; 40% | 1666; 44% | 1690; 16% |
| IIZKDo | 1658; 18% | 1666; 64% | 1690; 18% |

Figure 7:
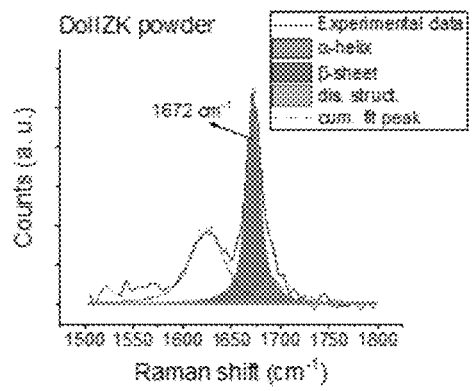
FIG. 7 is a graph showing the Raman spectroscopy of DoIIZK in powder form according to an embodiment of the present disclosure.
Figure 8:
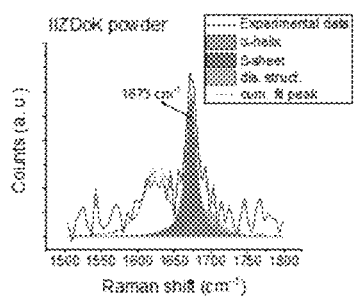
FIG. 8 is a graph showing the Raman spectroscopy of IIZDoK in powder form according to an embodiment of the present disclosure.
Figure 9:
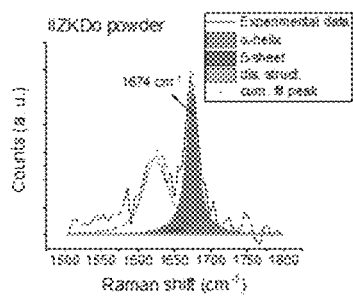
FIG. 9 is a graph showing the Raman spectroscopy of IIZKDo in powder form according to an embodiment of the present disclosure.

In one embodiment, the three peptides in powder form showed only the presence of β-sheets. The Raman spectroscopy signatures of the three peptides in powder form are shown in FIGS. 7-9.

In one embodiment, the solvent impacts the nanofibrous physico-chemical characteristic of the hydrogel. The importance of solvent on nanofibrous physico-chemical characteristic of the hydrogel is evidenced by the structural differences of hydrogels in 1×PBS and in powder form.

The Nanofibrous Morphology of Self-Assembling Peptides

In one embodiment, the nanofibrous morphology of the self-assembling peptides is affected by the position of Dopa. This impact of Dopa position on structure is further confirmed by the SEM and AFM microscopy images.

Figure 10:
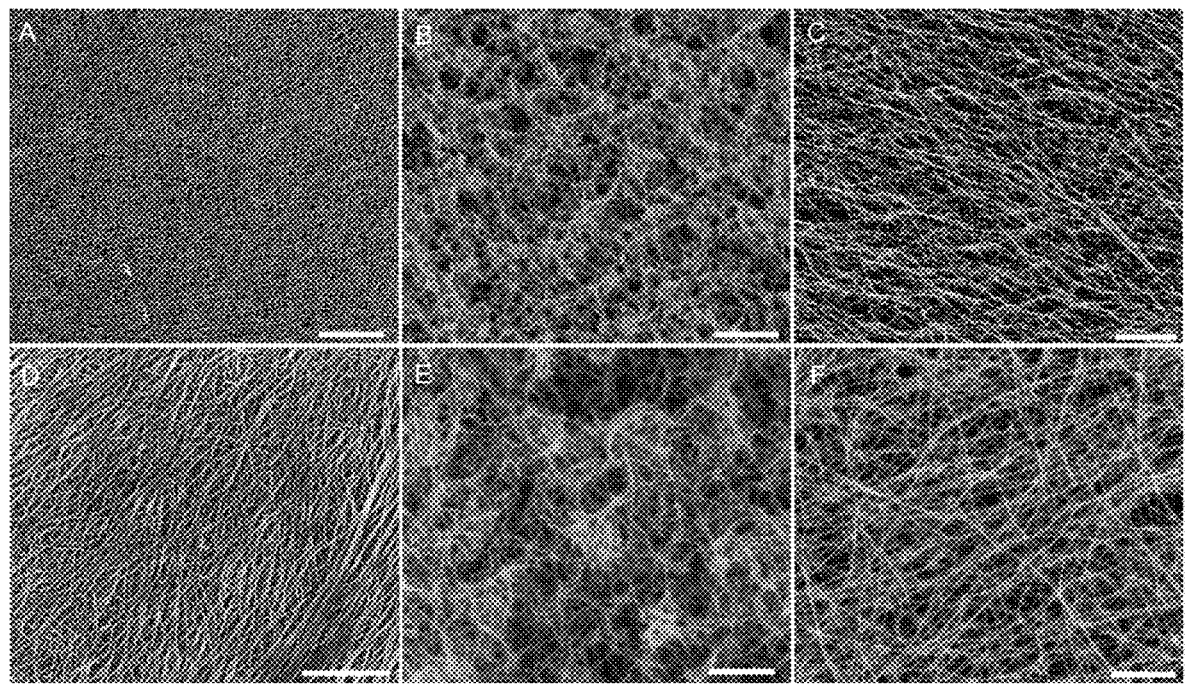
FIG. 10 is a scanning electron micrograph showing the nanofibrous structure of DoIIZK, IIZDoK, and IIZKDo according to an exemplary embodiment of the present disclosure.

FIG. 10 shows the SEM microscopy images of DoIIZK, IIZDoK, and IIZKDo. The scalebars in panels A, B and C are 2 μm, while the scalebars in panels D, E and F are 1 μm. As shown in FIG. 10, the fibrous structures of these peptides is similar to the fibrous structure of extra-cellular matrix in terms of mesh architecture. In FIG. 10, panel A and D shows the fibrous structures of DoIIZK, panel B and E shows the fibrous structures of IIZDoK and panel C and F shows the fibrous structures of IIZKDo.

In one embodiment, the hydrogels formed by DoIIZK, IIZDoK, and IIZKDo show some difference in fibrillar features. As shown in panels A and D of FIG. 10, the fibrils of DoIIZK and IIZKDo form clear network of fibers. On the other hand IIZDoK does not have clearly defined fibers.

In one embodiment, the position of Dopa affects peptide self-assembly. When Dopa is located in C-terminus or N-terminus, the peptides are more likely to self-assemble into compact network than when Dopa is located in the middle of the peptide sequence.

All these results point to the influential role that the position of Dopa plays in peptide fibril-water interaction in hydrogelation.

Figure 11:
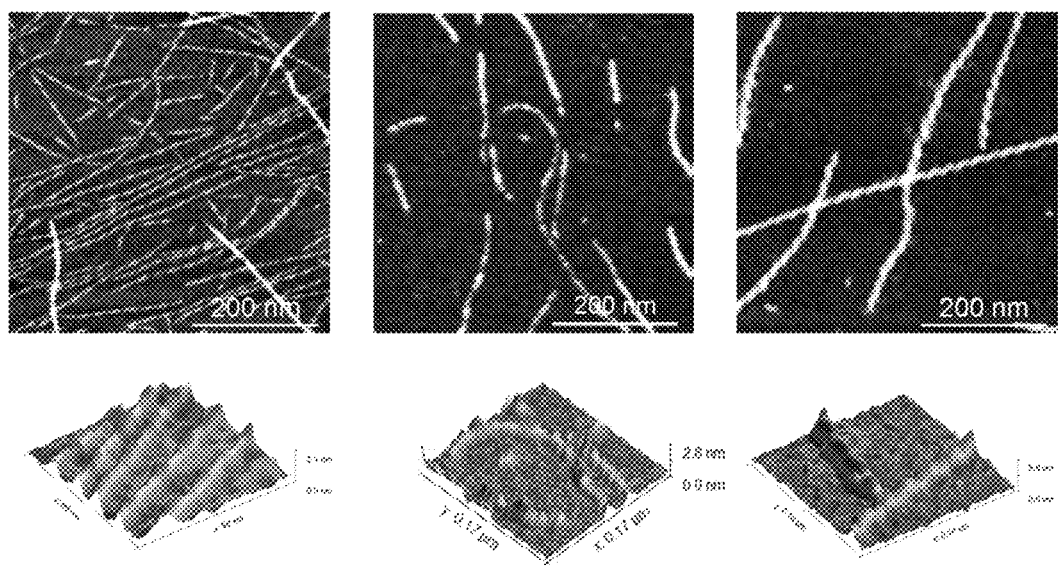
FIG. 11 is AFM topography with corresponding 3D plot showing the nanofibrous structure of DoIIZK, IIZDoK, and IIZKDo according to an exemplary embodiment of the present disclosure.
Figure 12:
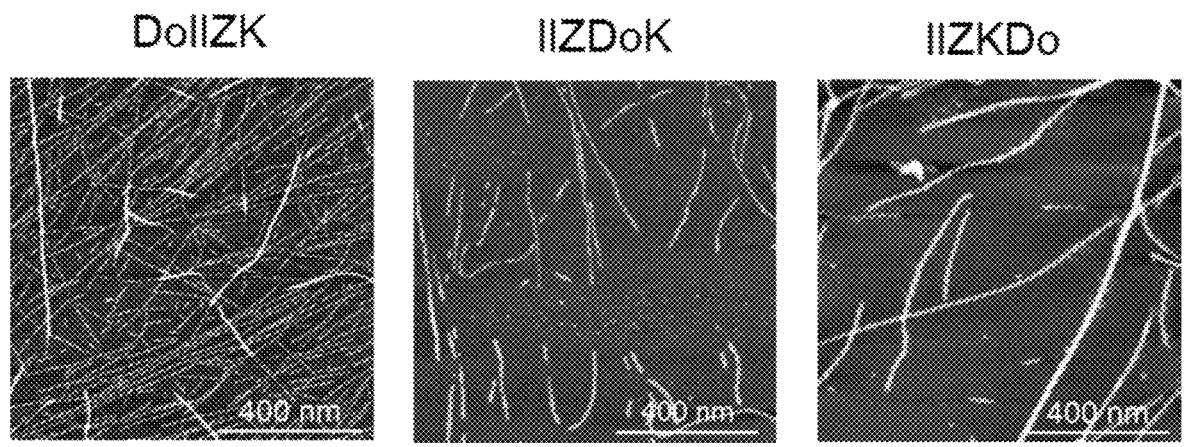
FIG. 12 is enlarged AFM topography showing the nanofibrous structure of DoIIZK, IIZDoK, and IIZKDo according to an exemplary embodiment of the present disclosure.

In one embodiment, DoIIZK and IIZKDo form nice long and twisted fibers whereas, but IIZDoK peptide performs scarcely even at the concentration of 10 mg/mL. In particular the morphological properties are evidenced by the AFM topography as shown in FIGS. 11 and 12. The photos in FIG. 11 has a scalebar of 200 nm, while the photos in FIG. 12 has a scalebar of 400 nm. The peptides shown in FIGS. 11 and 12 are dissolved in MilliQ® water at the concentration of 13 mM. According to the AFM photos in FIGS. 15 and 16 and 3D plot shown in FIG. 11, peptides DoIIZK, IIZDoK and IIZKDo show the following structural properties:

DoIIZK: helical pitch of 24.75±1.46 nm; maximum diametre 1.01±0.14 nm; minimum diametre: 0.66±0.09 nm.

IIZDoK: helical pitch of 8.63±0.49 nm; maximum diametre 1.66±0.19 nm; minimum diametre: 1.16±0.17 nm.

IIZKDo: helical pitch of 24.21±1.24 nm; maximum diametre 3.87±0.28 nm; minimum diametre: 3.09±0.16 nm.

Therefore, the peptides with the Dopa at either ends have similar features also in terms of fibre topography.

The Stiffness of the Peptide Hydrogels

Figure 13:
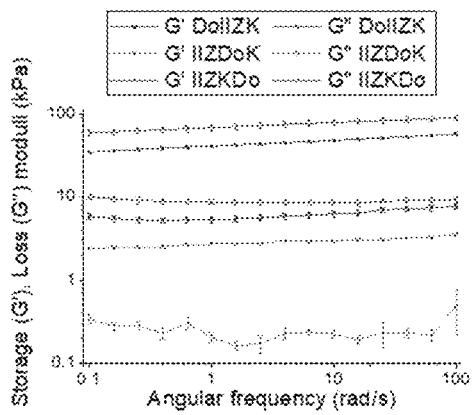
FIG. 13 is a graph showing the Rheology characterization of DoIIZK, IIZDoK.

In one embodiment, the structural characteristics of these peptides also influence the rheological properties of the peptides, such as stiffness. The stiffness of the peptide hydrogels was assessed by rheology measurements. The five peptides, DoIIZK, IIZDoK, IIZKDo, IIZ(KDo)$_2$ and IIZ(KDo)$_3$ were dispersed in phosphate-buffered saline (1×PBS) to final concentrations of 10 mg/mL. Only DoIIZK and IIZKDo formed transparent hydrogels after preparation of gels onto rheology glass rings; the rest of the peptides formed grey/opaque hydrogels. This difference implies that the fibrils of peptides DoIIZK and IIZKDo had sufficient time to disperse and spread in solution before entrapping water to gel, while peptides IIZDoK, IIZ(KDo)$_2$ and IIZ(KDo)$_3$ gelled quickly upon fibril formation. Therefore, the rheological properties of the peptides were measured at the concentration of 15 mg/ml. In one embodiment, rheological studies showed that the hydrogels formed by DoIIZK, IIZDoK, and IIZKDo exhibited a range of Storage moduli from 5 kPa to 100 kPa, as shown in FIG. 13. The storage modulus and loss modulus reflect the stress response of the hydrogel in oscillatory shear. A visco-elastic response is a mixture of both storage modulus and loss modulus. The storage modulus is the elastic solid-like behaviour (G'), whereas the loss modulus is the viscous response (G"). DoIIZK and IIZKDo, exhibited both higher values of Storage and Loss moduli as compared to IIZDoK which shows roughly 10 times lower values in comparison, also as shown in FIG. 13. In particular, DoIIZK and IIZKDo show values of Storage modulus going from 30 to 80 kPa, with the IIZKDo bearing the higher values, while IIZDoK shows values around 2-5 kPa.

In one embodiment, DoIIZK, IIZDoK, and IIZKDo show outstanding difference in Storage modulus, when compared to their original IIZK. The comparison of Storage modulus between Dopa peptides and IIZK is shown in FIG. 14.

The loss factor (tan δ), expressing loss/storage moduli, evidences a degree of resistance to oscillation strain. In one embodiment, the hydrogel of DoIIZK has a higher loss factor than the hydrogel of IIZKDo, which has a higher loss factor than the hydrogel of IIZDoK. FIGS. 15-19 show the Storage modulus, Loss modulus and Loss factor of the three catechol peptide hydrogels at different oscillation strains.

Molecular Dynamic Simulations (MD) of the self-assembly process of each peptide in water confirmed the experimental findings described above. Two cases were considered for each kind of peptide, 4- and 60-peptides assembly.

FIG. 20 shows the 60-peptides assembly simulation results. As shown in FIG. 21, all three peptides can form a single, stable fiber without breaking apart in 100 ns. Considering the periodic boundary conditions of the simulation box, the fibers can be formed infinitely long along an axis from the monomers.

The density map of the fibers was retrieved from the MD simulation. The density maps of DoIIZK, IIZDoK, and IIZKDo are shown in panels a, b and c of FIG. 21, respectively. FIG. 21 shows the density maps and water distribution of DoIIZK, IIZDoK, and IIZKDo. Panels a and d of FIG. 21 show the density maps and water distribution of DoIIZK, respectively; Panels b and e of FIG. 21 show the density maps and water distribution of IIZDoK, respectively; and Panels c and f of FIG. 21 show the density maps and water distribution of IZZKDo, respectively. The fiber dimensions shown in panels a, b and c of FIG. 21 was estimated based on fibers along the plane perpendicular to fiber axis.

According to panels a, b and c of FIG. 21, the diameter of the fibers increase in the order of DoIIZK<IIZDoK<IIZKDo, which is consistent with the findings show in the AFM topography shown in FIG. 11.

In one embodiment, the distinctive fibrous structure formed by Dopa peptides allows the resulting gel to entrap water, which consist at least 99% of the volume of the hydrogels.

According to panel d of FIG. 21, the larger diameter of the IIZKDo peptide is due to the higher water penetration in its fibers structure. According to panels d, e and f of FIG. 21, the water penetration into DoIIZK and IIZDoK peptides is minimal, with most of the water molecules forms around the fiber. In the case of IIZKDo instead, water penetration into the fiber is enhanced.

The local assembly behaviour of the peptides is characterized using 4-peptides and 60-peptides assembly simulations.

The snapshots from the 4-peptides assembly simulation at different time points are shown in FIGS. 22-24. At t=0, the peptides are placed dispersedly in the water box. The pair formation times these peptides are 0.9 ns for DoIIZK shown in FIG. 22, 2.0 ns for IIZDoK shown in FIG. 23 and 1.6 ns for IIZKDo shown in FIG. 24, respectively. The peptide has shorter pair formation time also has shorter gelation time. Therefore, the 4-peptides assembly simulation greatly supports the gelation time results of the peptides.

The cluster formation times of these peptides are 3.0 ns for DoIIZK shown in FIG. 22, 7.0 ns for IIZDoK shown in FIG. 23 and 6.5 ns for IIZKDo shown in FIG. 24. The peptide has shorter cluster formation time also has shorter gelation time. Therefore, the cluster formation time is again consistent with the gelation time of thee peptides. In other words, DoIIZK has the shortest gelation, pair formation and cluster formation time, followed by IIZKDo, while IIZDoK has the longest gelation, pair formation and cluster formation time.

In one embodiment, two major secondary structure conformations, antiparallel sheets and turns can be formed during the 4-peptides assembly simulation, in addition to pairs. The formation of antiparallel sheets and turns by DoIIZK, IIZKDo, and IIZDoK is shown in FIG. 25. The presence of these secondary structures illustrate by simulation is consistent with CD spectra shown in FIGS. 10-12 and Raman spectroscopy shown in FIGS. 4-6.

In one embodiment, the peptide assemblies are maintained by hydrogen bonds, as shown in the snapshot of the secondary structure. The table below summarizes the number of hydrogen bond formed in the different conformers with 4 peptides assembly in MD simulation:

|        | Antiparallel pairs | β-sheets | β-turns |
|--------|-------------------|----------|---------|
| DoIIZK | 2                 | 4        | 7       |
| IIZDoK | 0                 | 3        | 2       |
| IIZKDo | 0                 | 4        | 5       |

In one embodiment, DoIIZK and IIZKDo bear larger amount of hydrogen bonds in 4 peptides assembly, as shown in the table above.

In ene embodiment, during the process of simulation, most of the hydrogen bonds are inter-peptide rather than intra-peptide. The number of hydrogen bonds in the process of fibre formation by 60-peptides assembly was counted. FIG. 26 shows the analysis of hydrogen bonds count in the formation by 60-peptides assembly. The large number of inter-peptide hydrogen bonds further proves that the fibre is stabilized by inter-peptide hydrogen bonds.

In one embodiment, the hydrogels formed with Dopa peptides are suitable for underwater applications and preservation of a moist environment to leave the tissue hydrated without obstructing the pores, due to their ability of entrapping large amount of water.

In another embodiment, the self-assembly of Dopa peptides can be enhanced in the presence of phosphate buffer saline (PBS), which induces gelation similarity to sea water containing various salts.

In one embodiment, IIZ scaffold plays an important role to preserve hydrophobicity in the peptide sequence, while the incorporation of the Dopa residue is on either the N-terminus or the C-terminus of the IIZ scaffold.

In one embodiment, a lysine residue is also incorporated in the Dopa peptide sequent.

In one embodiment, the Dopa peptides may be used for low-cost, easy and efficient production of polymer-based hydrogels and adhesives, due to their short length.

Adhesion Measurements by AFM Force Spectroscopy

In one embodiment, adhesion measurements were performed in liquid by using Atomic force microscopy (AFM). In one embodiment, the measurement was taken in MilliQ® water. In another embodiment, the measurement was taken in 1×PBS.

In one embodiment, the peptides were dissolved in the proper solution at a concentration of 10 mg/mL. The peptide solutions were spotted on a freshly cleaved mica sheet and the measurement was performed in liquid.

In one embodiment, the adhesion properties of the Dopa peptides are influenced by the construct lysine-Dopa and by the position of the catechol moiety in the peptide sequence, as indicated by the AFM force spectroscopy results in liquid. A typical force-distance AFM curve to identify maximum adhesion force shown in FIG. 27. In a typical force spectroscopy curve the probe is several times approached to the surface and retracted and for every cycle of retraction the maximum force of adhesion is recorded. The incorporation of a catechol moiety near a lysine would enhance adhesion to negatively charged surfaces. FIG. 28 illustrates the effect of lysine on adhesion to negatively charged surfaces. Therefore, probes and substrates that were manifesting negative charges on their surfaces, such as the silicon probe and the freshly cleaved mica substrate, are used in the AFM spectroscopy. The setup of probe and substrate is illustrated in FIG. 29.

The peptides dissolved in the proper solution at 13 mM concentration each, were spotted on a freshly cleaved mica sheet and the measurement was performed in liquid. Several force curves were recorded for different buffers. FIG. 30 shows the AFM curves for DoIIZK, IIZKDo, and IIZDoK in MilliQ® water. In FIG. 30, the inset image represents the maximum extension of each peptide dissolved in water, when manually pulled between two glass slides. Also in FIG. 30, the approach part of the curve contains the important information defined as "jump to contact", while the retract part of the F-D curve contains the adhesion force value. FIG. 31 shows the AFM curves for DoIIZK, IIZKDo, and IIZDoK in other buffer solutions, including 137 mM NaCl, 10 mM $PO_4$, and 1×PBS. Furthermore, the AFM results were plotted as box plots, shown in FIG. 32. Two controls were also introduced: namely the original peptide IIZK, and an alternative peptide IIFK. To better understand the influence of Dopa on the adhesion properties of the peptide, the original short peptide IIZK would make a perfect negative control. We also introduced as a control the IIFK peptide in order to understand the effect of IIZK itself on adhesion. In FIG. 32, statistical significance expressed as $p<0.01$.

The approach part of the force spectroscopy curves is different for the three peptides, as shown in FIG. 30. DoIZK and IIZDoK have a negative peak, called "jump to contact", indicating attractive forces, including mostly electrostatic and van der Waals forces, between the sample and the probe[48,49]. This feature mostly disappears upon addition of ionic species in solution, as shown in FIG. 31. This finding also supports the cohesive behaviour found in the macroscale measurements, which is greater in MilliQ® water, free of ionic species.

Several considerations on the molecules and solutions used are also important: at pH below 10, the catechol ring is always protonated and lysine is positively charged below pH 9. Therefore, lysine can exert its wiping effect at the pH of these experiments, which were conducted at pH lower than 9. On the other hand, because the physiological solution is rich in ionic species, such as NaCl, the effect of the ionic strength on the adhesion properties of these peptides was also determined.

In FIG. 32, which plotted the results of these AFM measurements as box charts, the peptide' behaviour, in terms of adhesion force, is compared in the same solvent. FIG. 33 shows the behaviour of the single molecules in the different solvents. In FIG. 33, the peptides were dissolved at the concentration of 13 mM. The Geometric means and Geometric standard deviations of the AFM measurements for DoIIZK, IIZDoK, IIZKDo, IIFK, and IIZK in different solvents are summarized in the table below:

| Peptide | Force of adhesion (Geometric Mean (PN)) | Geometric SD (PN) |
|---------|-----------------------------------------|-------------------|
| DoIIZK MilliQ® | 112.72873 | 3.18399 |
| DoIIZK $PO_4$ | 34.81309 | 4.83868 |
| DoIIZK NaCl | 64.64315 | 2.40183 |
| DoIIZK 1 × PBS | 13.36265 | 5.22007 |
| IIZDoK MilliQ® | 71.99589 | 3.34308 |
| IIZDoK $PO_4$ | 22.47497 | 5.91616 |
| IIZDoK NaCl | 44.00825 | 3.19562 |
| IIZDoK 1 × PBS | 23.32646 | 4.50138 |
| IIZKDo MilliQ® | 73.31282 | 3.94791 |
| IIZKDo $PO_4$ | 13.89437 | 5.41282 |
| IIZKDo NaCl | 76.88595 | 4.75704 |
| IIZKDo 1 × PBS | 29.5645 | 4.82805 |
| IIZK MilliQ® | 75.66126 | 4.56028 |
| IIZK $PO_4$ | 5.68067 | 194.42389 |
| IIZK NaCl | 100.41019 | 2.84247 |
| IIZK 1 × PBS | 11.5885 | 5.33266 |
| IIFK MilliQ® | 89.76872 | 3.92885 |

| Peptide | Force of adhesion (Geometric Mean (PN)) | Geometric SD (PN) |
|---|---|---|
| IIFK PO$_4$ | 8.35819 | 4.31078 |
| IIFK NaCl | 13.217 | 5.79604 |
| IIFK 1 × PBS | 12.13308 | 3.84661 |

The addition of NaCl to IIZK increased the adhesion force by 20%. The addition of both NaCl and PO$_4$ strongly decrease the adhesion values of IIFK which were reduced by about 80%.

In one embodiment, Dopa modified IIZK peptides are affected by the addition of salts and PO$_4$.

In one embodiment, the addition of NaCl reduced the adhesion force of DoIIZK and IIZDoK by about 50%. However, NaCl did not significantly impact the adhesion force of IIZKDo.

In one embodiment, the addition of PO$_4$ reduced the adhesion force of DoIIZK, IIZDoK and IIZKDo to a greater extent than NaCl.

In one embodiment, the effect of 1×PBS addition is, in general, to further reduce the adhesion values of DoIIZK, IIZDoK and IIZKDo, compared to NaCl.

In one embodiment, a decrease in adhesion is observed upon addition of ionic species also in the peptides not containing Dopa in most cases. This effect is likely due to the screening of the charges provided by monovalent and polyvalent salt ions.

However, the reduction of adhesion forces by the addition of ionic species is much less consistent in IIZK than IIFK.

In one embodiment, IIZKDo peptide conserved more adhesive properties than DoIIZK, IIZDoK in NaCl and 1×PBS.

In one embodiment, PO$_4$ buffer reduced the adhesion forces of all peptides to a greater extend, compared to NaCl and 1×PBS. The greater effect of PO$_4$ buffer in reducing the adhesion is due to the changes of both pH and the size of the ionic species. The presence of more negatively charged species in solution due to increased pH and the large counter-ion PO$_4$ is very likely screening the lysine residues of the amphiphilic peptides, therefore the interaction with the AFM probe surface is reduced. In the case of solution containing NaCl, which has lower pH, it is possible that both the diminished presence of negatively charged species and the small size of the Cl$^-$ ion, contribute to the charge screening on the peptides' surface to a less extent, therefore affecting much less the overall adhesion.

In one embodiment, the position of Dopa at the C-terminus of IIZK is desirable, because the IIZK sequence is preserved, therefore allowing to keep the adhesion effect intact, even though the vicinity of the catechol moiety to the lysine contributes to the screening effect nearby the Dopa molecule.

In one embodiment, the addition of the catechol moiety to the ultrashort self-assembly peptide IIZK has the positive effect of increasing its adhesive properties in physiological solution, when Dopa is in the terminal position aside of lysine.

In one embodiment, the ionic species will screen the charges of the peptides in solution therefore reducing the cohesion forces between the peptides.

In one embodiment, the peptides show higher cohesive forces in MilliQ® water, because the hydrogen bonds and weak interaction forces are effective in maintaining the cooperative intermolecular adhesion when the peptides are dissolved in MilliQ® water.

In one embodiment, the more hydrogen bonds formed, the greater the adhesion forces of the peptide. The difference of adhesion among peptides DoIIZK, IIZDoK and IIZKDo in MilliQ® water is supported by the MD simulation, which reports higher number of hydrogen bonds in DoIIZK.

In one embodiment, the intermolecular cohesion of IIZKDo is lower, because a larger portion of the hydrogen bonds formed in IIZKDo are intramolecular, compared to DoIIZK and IIZDoK. As shown in FIG. 26, the number of intramolecular hydrogen bonds in IIZKDo is slightly higher than in the other two peptides, therefore explaining the lower intermolecular cohesion of this peptide.

In one embodiment, the presence of nanofibres attached to the substrate during force spectroscopy measurement was verified by AFM topography, as shown in FIG. 34. The nanofibers are always present in all the buffer conditions, due to the high molarity of the solution.

Cell Viability Results

In one embodiment, the Dopa peptides are cytocompatible and are suitability for 3D tissue printing, tissue engineering, surgical applications and glue, due to their gel and glue properties.

In one embodiment, cytocompatibility of the peptide nanogels was evaluated using mouse myoblast cells (C2C12). After 24 hours of incubation, cell proliferation was tested with DoIIZK, IIZDoK, IIZKDo, IIZ(KDo)$_2$ and IIZ(KDo)$_3$ at a concentration of 3 mg/mL to evaluate biocompatibility. The MTT (3-(4,5-dimethylthiazol-2-yl)-2,5-diphenyltetrazolium bromide) assay was used in order to quantify the number of viable cells. In one embodiment, a standard curve for a known number of cells was also plotted. In one embodiment, the test results were compared to the positive control 2D culture. A positive indication of cytocompatibility would be the survival of the cells following incubation with the peptides. For comparison, peptides DoIIZK, IIZDoK, IIZKDo, IIZ(KDo)$_2$ and IIZ(KDo)$_3$ were tested as part of the study. The cytocompatibilty of all peptides tested was evaluated by quantifying the survival cells by visualising the live/dead cells using calcein AM and Ethidium bromide staining.

In one embodiment, peptides DoIIZK, IIZDoK, IIZKDo, and IIZ(KDo)$_2$ grow well into the tissue constructs.

In one embodiment, exposure of C2C12 cells to DoIIZK, IIZDoK, and IIZKDo, and IIZ(KDo)$_2$ nanogels with a concentration of 3 mg/mL did not affect cell growth for any of the peptides.

The in vitro culturing of C2C12 cells with peptides DoIIZK, IIZDoK, IIZKDo, and IIZ(KDo)$_2$ demonstrated that exposure of C2C12 to a concentration of 3 mg/mL of peptide nanogels did not affect cell growth for any of the peptides, when compared to cell growth in 2D tissue culture plates for positive control. The cytocompatibility results were shown in FIG. 35. The growth of C2C12 cells was reflected by live/dead staining, as shown in FIG. 35. Poli-D Lysine (PDL) was used for 2D control. The scalebar in FIG. 35 is 200 μm. Cytocompatibility of all peptides was evaluated by quantifying the survival cells by visualising the live/dead cells using calcein AM and Ethidium homodimer staining. The live cells are stained green by calcein AM, while the dead cells are stained red by Ethidium homodimer.

The cytocompatibility of the hydrogel formed by IIZ(KDo)$_3$ is significantly different from that of 2D culture, ash shown in the last row of FIG. 35. Therefore, DoIIZK, IIZDoK, and IIZKDo, IIZ(KDo)$_2$ scaffolds are suitable and biocompatible with C2C12 cells, while IIZ(KDo)$_3$ is not biocompatible.

In one embodiment, exposure of C2C12 cells to IIZ (KDo)$_3$ nanogel with a concentration of 3 mg/mL reduced cell growth.

In one embodiment, the cells grown in DoIIZK, IIZDoK, and IIZKDo, and IIZ(KDo)$_2$ nanogels were metabolically active for up to day 21.

In one embodiment, cells cultured in DoIIZK, IIZDoK, and IIZKDo, and IIZ(KDo)$_2$ nanogels demonstrated good viability at various concentrations up to the solubility limit of the peptides. However, IIZ(KDo)$_3$ was toxic for the cells.

In one embodiment, the metabolic activity of cells cultured in DoIIZK, IIZDoK, and IIZKDo, and IIZ(KDo)$_2$ nanogels was consistently comparable to 2D cultures (cells in absence of peptides). Fluorescence imaging of the hASCs stained with calcein AM and ethidium homodimer showed that the cells are metabolically active, as indicated by the presence of calcein fluorescence in the cells, and that the cellular membranes were intact, as indicated by the absence of ethidium bromide fluorescence in the cells.

The Application of Dopa-Peptides as Glue

In one embodiment, the Dopa peptides were used to glue coral fragments to tiles and 3D printed skeleton structure and can preserve the healthy status of the glued coral. Therefore, the Dopa peptides can be applied in coral reef restoration projects.

Corals are perhaps the most important member of the shallow water undersea world. The total surface area of all coral reefs on the earth is less than 1% of the total marine environment, and yet manage to provide food and shelter to over one quarter of all marine species in the ocean. Moreover, 90% of the oxygen from the sea comes from the corals.[50] However, climate change, pollution, overfishing and destructive fishing, invasive species are a continuous threat for the survival of this delicate ecosystem. Several efforts are in place worldwide to maintain and enhance this complex ecosystem[51].

Often, small scale coral nurseries are put in place, where fragments of corals are attached to several types of supports[52-53]. The adhesion of corals to this type of support by the use of a biocompatible and eco-friendly glue is therefore needed.

In one embodiment, IIZKDo, the most adhesive three catechol peptides among DoIIZK, IIZDoK, and IIZKDo, was also the most effective glue in seawater, and was able to keep several coral fragments glued to a 3D printed substrate for several months, as shown in FIGS. 38-40. The donor corals Acropora spp. shown in FIG. 36 were collected from the Red Sea.

In one embodiment, coral fragments were attached to a tile using DoIIZK, IIZDoK, IIZKDo as a glue. The tile, to which the coral fragments were attached, has a size 10×10 cm and was placed into a shallow aquarium supplied with running seawater.

In one embodiment, the survival rate of the coral fragments fixed with DoIIZK was 67%, whereas the survival rate glued with IIZDoK and IIZKDo were respectively 0% and 100%, after 3 days. The 3-day survival data is summarized in the table below:

| Acropora fragments | n | Survival after attachment | Survival after 3 days in the aquarium |
|---|---|---|---|
| DoIIZK | 3 | 3 | 2 |
| IIZDoK | 3 | 3 | 0 |
| IIZKDo | 3 | 3 | 3 |

In one embodiment, IIZKDo is a better glue than DoIIZK, and IIZDoK.

In one embodiment, IIZKDo was used for the adhesion of bigger and heavier coral fragments to the 3D printed coral, which would be the situation in coral reef restoration. In gluing larger coral fragments, two different type of Acropora hemprichii were glued: some big fragments with an irregular base, and some smaller pieces with smooth base.

In one embodiment, the big fragments with irregular base and the smaller pieces with smooth base were attached to a tile. The cut small pieces of coral were attached to a special sheet for macrofragmentation so that these fragments further grew on the surface of the spreadsheet, in order to obtain fragments with a base smooth enough to stick them on the tile. After 15 days, the big fragments were still fully attached to the tile, whereas the small, flat fragments were all detached. The survival data of these fragments are summarized in the table below:

| Acropora fragments | n | Survival after attachment | Survival after 15 days in the aquarium |
|---|---|---|---|
| Big fragments | 5 | 5 | 5 |
| Flat fragments | 3 | 3 | 0 |

In one embodiment, the Dopa-peptide glue was used to stick the bigger fragments described above to the 3D printed coral construct in order to allow the coral to grow on the construct, as shown in FIG. 37.

In one embodiment, the 3D printed coral construct with glued coral fragments was use as a scaffold for coral reef restoration. The fragments remained firmly attached to the 3D scaffold even after 19 days, as shown in FIGS. 38 and 39.

Adhesive materials that are biocompatible, non-immunogenic and biodegradable are greatly desirable for medical intervention especially in internal surgery and wound healing, and in engineering/environmental applications performed underwater. Adhesive properties in wet, salty conditions are difficult to achieve, and the catechol moiety present in the foot proteins of the byssus of several sessile organisms has prompted an entire research field aimed at solving this issue, by investigating the properties of adhesive materials with the catechol moiety.

Hydrogels based on natural peptides have gained a lot of attention in recent years due to their ability to provide a 3D scaffold for cellular growth and due to their biodegradability. In particular, hydrogels formed by ultrashort self-assembling peptides (SAP) have proven high biocompatibility, tunability and suitable mechanical properties for several applications. The combination of these peptides with the adhesive molecule catechol could eventually provide a better outcome in terms of adhesiveness in wet, saline environment while keeping the positive characteristic of the SAP hydrogels.

In one embodiment, the present disclosure provided SAP peptides with adhesive properties, by incorporating catechol moiety. The adhesive properties of these SAPs were measured by AFM force spectroscopy.

In one embodiment, while the SAP peptide possess per se, some adhesive properties, in physiological conditions, the peptides' adhesive properties are enhanced when the Dopa peptide is flanking the lysine residue at the C-terminus of IIZK.

In one embodiment, the mechanical properties of these peptides are also affected by the presence of catechol moiety.

In one embodiment, the IIZKDo peptide, that has the highest adhesion in physiological solution and the highest storage modulus, compared to DoIIZK and IIZDoK, making the peptide suitable for bioprinting applications, where the mechanical stiffness of the hydrogel is very important.

In one embodiment, the adhesives peptide IIZKDo can be used to glue coral fragments on 3D printed scaffolds.

In one embodiment, IIZKDo is the most adhesive peptide under physiological condition according to results of AFM force spectroscopy experiments, and is also the one to guarantee best adhesion, for long term cultivation, in sea water environment, together with high biocompatibility.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Solid Phase Peptide Synthesis

All three peptides Ac-Ile-Ile-Cha-Lys-Dopa-NH$_2$ (IIZKDo), Ac-Ile-Ile-Cha-Dopa-Lys-NH$_2$ (IIZDoK) and Ac-Dopa-Ile-Ile-Cha-Lys-NH$_2$ (DoIIZK) were manually synthesized through fluorenylmethoxycarbonyl (Fmoc)-based solid-phase peptide synthesis using Fmoc-protected aminoacids and Rink-amide resin purchased from GL Biochem™.

IIZK and IIFK peptides were synthesied as described previously.[11] Briefly, Ac-Ile-Ile-Phe-Lys-NH$_2$ (IIFK), and =Ac-Ile-Ile-Cha-Lys-NH$_2$ (IIZK) peptides were synthesized by solid-phase peptide synthesis (SPPS) using CS136X CS Biopeptide synthesizer. The peptide coupling is conducted on rink amide resin by aging the resin in a mixture of TBTU (3 eq.), HOBt (3 eq.) DIPEA (6 eq.), and Fmoc-protected amino acid (3 eq.). Piperidine/DMF with concentration of 20% (v/v) is used to deprotect the fmoc group on the N-terminus of the peptide sequence to continue to the next coupling step. After coupling the last amino acid to the peptide sequence on the resin, the sequence is capped with an acetyl group. All of those steps are conducted inside the synthesizer. The resin is then transferred out of the synthesizer and cleaved with an acidic solution of TFA, TIS, and water for a minimum of 2 hrs. The peptide is subsequently collected in a round bottom flask. Afterward, cold diethyl ether is added to further induce peptide precipitation and left standing overnight at 4° C. The precipitated peptide is separated from the supernatant by centrifugation and kept in a vacuum desiccator for drying. The collected peptides are purified using Agilent 1260 Infinity Prep-HPLC with Zorbax® PrepHT SB-C18 column for 12 minutes at the flow rate of 20 mL/min. MilliQ® water and Acetonitrile containing 0.1% formic acid are used as mobile phases. The purity of the peptides is further analyzed by analytical LC-MS and NMR.

Other used chemicals were purchased from Sigma-Aldrich®. Coupling reactions were performed using Fmoc-protected amino acids (3 eq.) activated with 2-(1H-Benzotriazole-1-yl)-1,1,3,3-tetramethylaminium tetrafluoroborate (TBTU) (3 eq.), Hydroxybenzotriazole (HOBt) (3 eq.) and N, N-Diisopropylethylamine (DIPEA) (6 eq.) in DMF. Removal of Fmoc protecting groups was accomplished by 20% (v/v) piperidine/DMF solution for 20 min. After completion of the targeted sequence the peptides were acetylated at the N-terminus. Cleavage of the peptides from the resin was effected by a 95% Trifluororoacetic acid (TFA) solution containing 2.5% MilliQ® water and 2.5% Triisopropylsilane (TIPS) for 2 h. The peptide solution was then precipitated in cold diethyl ether, centrifuged and dried under vacuum. The crude peptides were purified to above 95% using an Agilent 1260 Infinity Prep-HPLC with Zorbax® PrepHT SB-C18 column.

Example 2

1D Nuclear Magnetic Resonance 1D ($^1$H) NMR spectra of all purified peptides were recorded using Bruker® Avance III 500 MHz NMR spectrometer equipped with a cryoprobe. The samples were dissolved 5 mg peptide powder in 700 µL of d6-DMSO, and transferred to an NMR tube for measurement.

Example 3

Peptide Gelation Studies

The peptide powder was dissolved in 0.90 mL of MilliQ® water and vortexed until fully dissolved. Then, 0.10 mL of 10×PBS buffer were added to the peptide solution to reach a final concentration of 1×PBS. Gelation of the solution in the vial was observed by vial inversion method. The time and critical gelation concentration (CGC) at which each peptide formed a hydrogel were recorded.

Example 4

Raman Spectroscopy

Raman spectroscopy measurements were performed on DoIIZK, IIZDoK and IIZKDo at 5 mg/mL concentration in 1×PBS buffer or on dry powder samples after deposition on CaF$_2$ slide. Witec Alpha 300 RA confocal Raman spectrometer equipped with Andor CCD camera (DU970N thermoelectrically cooled at −75° C.) was used to perform the Raman measurements in backscattered configuration. The samples were excited through a 50× objective (Zeiss® LD EC Epiplan-Neofluar) with linearly polarized 532 nm wavelength excitation laser. For the analysis, the spectra were cosmic rays removed, baseline subtracted with a polynomial of 5th order, and averaged after normalization to the 1450 cm$^{-1}$ peak intensity. Several Voigt functions were fitted setting the peaks at 1653±3, 1663±3 and 1680±3 cm$^{-1}$, corresponding to α-helix, β-turn and unordered β-turn respectively, with a FWHM set to a max value of 25 cm$^{-1}$. An additional peak at about 1635 cm$^{-1}$ was introduced into the fitting to account for contributions from water, lysine and isoleucine Raman shifts.[11]

Example 5

Rheological Studies of the Hydrogels

Peptide hydrogels were prepared by weighing the appropriate peptide amount of the lyophilized peptide powder in 2 mL glass-vials. The peptides were dissolved in MilliQ® water before being vortexed briefly to obtain a homogenous solution. Then a define volume of 10× Phosphate-Buffered Saline (PBS) was added to this peptide-water mixture in order to form the subsequent gel at the final concentration of 1×. Rheological analysis mechanical properties of the formed gels were assessed by using the TA Ares-G2 Rheometer with an 8 mm titanium parallel-plate geometry. The peptide gels were prepared in a 8 mm diameter coated Poly(methylmethacrylate) (PMMA) ring, which were later incubated inside a sealed tissue-culture dish at room temperature for 18 hours prior to measurements. All rheology tests were done in nine replicates for each peptide, corresponding to a volume of 150 μL and a concentration of 15 mg/mL in each Poly(methylmethacrylate) (PMMA) ring. The final volume ratio of peptide solution with 10×PBS was 9:1. The measurements were conducted at a 1.6 mm gap distance with a temperature of 25° C. Time-sweep, frequency-sweep, and amplitude-sweep, were measured for each sample to explore the mechanical stiffness of the gels. Time-sweep analysis was performed for 5 minutes at an angular frequency of 1 Hz and at 0.1% strain to observe both storage modulus (G') and loss modulus (G") before the next measurements. For this experiment, frequency sweep analysis was subsequently carried out by reducing the angular frequency from 100 to 0.1 Hz while keeping the strain at 0.1%. In the end, amplitude sweep analysis was carried out to observe the minimum value of the amplitude strain needed to break the gel construct. This test was performed with an angular frequency and strain of 1 Hz and 0.01%-100%, respectively.

Example 6

Scanning Electron Microscopy (SEM) Study of Peptides Fiber Structure

For sample preparation, a solution peptide at 10 mg/mL concentration dissolved in 900 μL of MilliQ® water was dropped on a glass slide and afterwards 100 μL 10×PBS were added. The peptide nanogels slides were sequentially dehydrated for 15 minutes each by immersing them in wells containing different ratios of ethanol/water e.g. 20%, 40%, 60%, 80% and 100% (v/v) ethanol solutions. Additional dehydration in 100% ethanol solution was accomplished by changing the absolute ethanol solution with a fresh one, first for 15 minutes, then the sample was moved to another absolute ethanol solution for two hours. The dehydrated samples were first placed into the critical point dryer (CPD) for evaporation, then were mounted onto SEM aluminium pin stubs, gluing them with conductive silver paste. Finally, the samples were sputter-coated with a 5 nm thick coating of Iridium to make the surfaces electrically conductive. Morphology of coated peptides was analyzed using a Scanning Electron Microscopy system (FEI Quanta 600 and Magellan, Thermofisher®) at 5 KeV acceleration voltage and 20 pA current.

Example 7

Atomic Force Microscopy (AFM) Measurements

AFM topography measurements were performed on a Dimension Icon SPM (Bruker®). The samples were prepared as follows: peptides were dissolved at 13 mM concentration in MilliQ® water; after 30 minutes, 20 μl of these solutions were dropped on freshly cleaved mica sheets and immediately dried with an $N_2$ stream. Measurements were immediately performed in tapping mode in air by the use of an AFM probe AC_240TS_R3 (Olympus®) with nominal free oscillation at roughly 70 kHz and a nominal spring constant of 2 N/m. The probe was calibrated by contact-free method.[54] Free oscillation amplitude was set at 200 mV with a 5% damping during tapping mode measurement. AFM adhesion measurements were performed on a JPK Nanowizard™ III mounted on Olympus® IX-81 inverted optical microscope. A mica sheet was glued one day before the experiment with double component epoxy glue to a glass slide and enclosed in a plastic o-ring provided by the JPK company for liquid measurements. Each peptide was dissolved in MilliQ® water at a concentration of 13 mM and mixed gently. Starting with the measurement in MilliQ® water, 50 μL of the solution were dropped on the freshly cleaved mica sheet within 5 minutes from the preparation of the solution and let equilibrate for 10 minutes. After, the excess solution was removed by pipetting and discarded. Then 1 mL of MilliQ® water was added gently from the side and after 5 minutes, the sample was rinsed 3 times by additional 1 mL MilliQ® water. Finally, the sample was measured by AFM force spectroscopy (Quantitative imaging mode) with additional 1 mL MilliQ® water. The MilliQ® water was exchanged after the measurement alternatively with a water solution containing 137 mM NaCl or 10 mM Phosphate ions (a combination of $Na_2HPO_4 \cdot 7H_2O$ and $NaH_2PO_4 \cdot H_2O$ to reach pH 7.4). After performing the force spectroscopy map in these two different solutions, eventually, the liquid was exchanged with 1×PBS pH 7.4. To verify the presence of eventual fibers, after the measurement, the excess solution was removed by pipetting and discarded. The sample was then rinsed two times with 1 mL MilliQ® water and dried overnight in a vacuum chamber. The topography AFM imaging was performed using AC-240TS_R3 AFM probes in tapping mode in the JPK AFM.

For the adhesion measurements in liquid, XSC11-AlBS (MikroMasch®, GmbH) probe A was used, with nominal spring constant of 0.2 N/m and free oscillation frequency in air of 15 kHz. The probe was calibrated by contact-free method in liquid.[55] Quantitative imaging was performed by using the following parameters: force setpoint 1 nN, Z length 50 nm, velocity 75 μm/s, on a 2×2 μm area and 128×128 points. The height of the sample was verified to be always about 8 nm while performing the measurements, in order to have a uniform indentation for all the samples. 3 maps per sample were acquired. The force spectroscopy curves in the maps were analyzed with the proprietary JPK software. After correction for the bending of the cantilever, the adhesion value for each spectroscopy curve was identified as the point in the retract curve showing the minimum of force value and averaged, as illustrated in FIG. 27. Statistical analysis for the discrimination of the populations was performed with Kruskal-Wallis ANOVA for non-parametric tests and post-hoc test.

Example 8

Computer Simulations

Molecular dynamics simulations of DoIIZK, IIZDoK, and IIZKDo peptides self-assembly were performed in water to study the fiber formation on the atomic scale. The simulations were conducted by GROMACS 2018 with OPLS force-field.[56] The parameters for simulation boxes were summarized in the tables below:

| 4-peptide assembly | | | |
|---|---|---|---|
| | DoIIZK | IIZDoK | IIZKDo |
| Box size | 5.0 | 5.0 | 5.0 |
| Number of Water | 3901 | 3899 | 3883 |
| Number of Peptides | 4 | 4 | 4 |
| Net Charge in peptide | 0 | 0 | 0 |
| Mole Fraction | 0.001 | 0.001 | 0.001 |
| Speed on Shaheen | 147 ns/1 day/ 128 cores | 147 ns/1 day/ 128 cores | 147 ns/1 day/ 128 cores |

| 60-peptide assembly | | | |
|---|---|---|---|
| | DoIIZK | IIZDoK | IIZKDo |
| Box size | 9.9 | 9.5 | 9.5 |
| Number of Water | 29253 | 24788 | 24782 |
| Number of Peptides | 60 | 60 | 60 |
| Net Charge in peptide | 0 | 0 | 0 |
| Mole Fraction | 0.0021 | 0.0024 | 0.0024 |
| Speed on Shaheen | 174 ns/1 day/ 512 cores | 180 ns/1 day/ 512 cores | 180 ns/1 day/ 512 cores |

The topology parameter for the unnatural amino acid (Cha) was obtained by LigParGen webserver.[57] The SPC/E model was employed for water molecules. The integration of the equations of motion was conducted at a time step of 2 fs. All cases were done with periodic boundary conditions in a cubic simulation box. The long-ranged electrostatic interactions were handled by Particle Mesh Ewald Method;[58] the short-ranged non-bonded interactions cutoff value was 1.4 nm. There are three steps for MD simulation: energy minimization, equilibration and production MD. In the energy minimization, the structure of peptides was relaxed through this process in order to get reasonable starting structures. The equilibration step was conducted in two phases, the first phase was conducted under an isothermal-isochoric ensemble (NVT ensemble) to stabilize the temperature of the system; the second phase was conducted under an isothermal-isobaric ensemble (NPT ensemble) to stabilize the pressure of the system. The production MD system was coupled to a Berendsen Barostat[59] with reference pressure at 1 bar and a V-Rescale Thermostat® with reference temperature at 300 K. The total simulation time for all investigated peptides was 100 ns. Calculations were performed on 512 Intel® Haswell cores at 2.3 GHz.

During the simulation, two cases were considered for each of the peptides: 4-peptides assembly and 60-peptides assembly. The peptides were initially placed evenly in the simulation box and solvated with water.

Example 9

Cell Culture and Growth Conditions of Mouse Myoblast Cells (C2C12)

For mouse myoblast cells (C2C12) culture expansion, C2C12 cells were cultured either in a T175 or T75 culture flask in complete DMEM media (10% FBS and 1% P/S). The cells were placed in a humidified incubator at 37° C., with 95% air and 5% $CO_2$. Then they were subcultured using trypsin at approximately 80% confluence. Fresh culture media was added every 48 h to each well, after removing the previous media.

Example 10

3D Culture of Mouse Myoblast Cells in Peptide Hydrogels

For 3D culture of mouse myoblast cells in peptide hydrogels and cell viability assay, C2C12 cells were encapsulated in peptide hydrogels in a 96-well plate.[61] Briefly, peptide solutions DopaIIZK, IIZDopaK, IIZKDopa (3 mg/mL) were added to 40 µL/well. Mouse myoblast cells (30,000 cells/well) that were re-suspended in 2×PBS were then, mixed gently with the peptide solutions. The gelation time was 1-3 min for all 5 peptides. Subsequently, the culture medium was added to the wells.

The viability of 3D cultured cells was assessed using the LIVE/DEAD Viability/Cytotoxicity Kit (ThermoFisher®, USA)[11]. Calcein acetoxymethyl ester (Calcein-AM) is used to detect viable cells and ethidium homodimer-I (EthD-I) is used to detect dead cells. Briefly, staining with 2 µM of Calcein-AM and 4 µM of EthD-1 is performed after washing with Dulbecco's phosphate-buffered saline (D-PBS). After 30 minutes incubation, the staining solution was discarded, and 1×D-PBS was added to each well before imaging. Stained cells were imaged with an inverted confocal microscope (Zeiss® LSM 710 Inverted Confocal Microscope, Germany) or ZEISS® fluorescent microscope.

Example 11

Procedure for Selection of Best Glue and Coral Fragment Adhesion in Coral Restoration Applications The different glues were prepared at the same concentration of 40 mg/mL for DoIIZK, IIZDoK and IIZKDo. Then, the coral fragments were adhered to the surface of the tiles by applying gentle pressure as following: triplicates in the first line with DoIIZK as a glue, second line with IIZDoK and last line with IIZKDo. The experiment setup is illustrated in FIG. 40. The tiles were afterwards placed underwater in a tank containing filtered sea water. Only the three fragments that were glued using IIZKDo were still all sticking to the tile after 17 days, as shown in FIG. 40. One of the fragments that was glued with DoIIZK detached less than 15 minutes after we placed the tile under water and all of the fragments that were glued with IIZDoK detached around 30 minutes after they have been placed under water.

After verifying the best performing glue among the three DoIIZK, IIZDoK, IIZKDo, IIZKDo was selected to glue some coral fragments onto 3D printed PLA corals used for coral reef restoration project. Using a diagonal plier, the tip of each branch-like part (ca. 1.5-2.5 cm in length) of a donor *Acropora hemprichii* coral was gently cut to minimize damage to the coral itself. FIG. 36 illustrates the parts being cut from the donor coral. FIG. 41 shows the tip got cut. The initial donor coral was moved from a large shallow aquarium (230×148×140 cm) supplied with running seawater to a relatively shallow aquarium also outfitted with running seawater. While preparing the glue, the cut fragments were kept in a small shallow aquarium (72×54×29 cm) filled with sea water to not harm them until use. In the meantime, the glue was prepared by mixing IIZKDo 40 mg/mL in water and the mixture was poured on a glass slide and allowed to rest for about 5 minutes to equilibrate, as shown in FIG. 42. The cut coral fragment was removed from the aquarium, and cleaned, while moisture was allowed to absorb from the cut section with sterilized filter paper. The ceramic tile was cleaned twice with water, and then sea water to mimic the adhesion of the glue to a wet, salty surface.

A few drops of IIZKDo was applied at the surface of the cut section of the coral fragment, and the fragment was immediately glued at the surface of the tile, as shown in FIG. 43. As a control, some smaller fragments with smooth surface *Acropora hemprichii*, were glued using the same peptide-based glue.

The tile with attached coral fragments was placed in the original shallow aquarium (230×148×140 cm) to keep the coral in its natural environment as shown in FIG. 44 and checked after 3 days. Only the big fragments were still sticking on the tile. Therefore, only big fragments were then glued to the 3D printed poly-lactic acid (PLA) printed coral structure primed with MakerBot, which is a 3D printer based on fused deposition modeling method and grew in harsher conditions, such as in the presence of algae etc. The 3D printed coral skeleton is shown in FIG. 45.

It is intended that the invention not be limited to the particular embodiment disclosed herein contemplated for carrying out this invention, but that the invention will include all embodiments falling within the scope of the claims.

All documents, patents, journal articles and other materials cited in the present application are incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

REFERENCES

The following references are referred to above and are incorporated herein by reference:

1. R. Pérez-Pedroza, A. Ávila-Ramírez, Z. Khan, M. Moretti, C. A. E. Hauser, *Advances in Polymer Technology* 2021, 2021, 8815006.
2. S. Abdelrahman, M. Alghrably, J. I. Lachowicz, A.-H. Emwas, C. A. E. Hauser, M. Jaremko, *Molecules* 2020, 25.
3. A. P. Duarte, J. F. Coelho, J. C. Bordado, M. T. Cidade, M. H. Gil, *Progress in Polymer Science* 2012, 37, 1031-1050.
4. H. Zhu, J. Tian, H. Mao, Z. Gu, *Current Opinion in Biomedical Engineering* 2021, 18, 100271.
5. C. A. Hauser, R. Deng, A. Mishra, Y. Loo, U. Khoe, F. Zhuang, D. W. Cheong, A. Accardo, M. B. Sullivan, C. Riekel, J. Y. Ying, U. A. Hauser, *Proc Natl Acad Sci USA* 2011, 108, 1361-1366.
6. N. Wiradharma, U. Khoe, C. A. E. Hauser, S. V. Seow, S. Zhang, Y.-Y. Yang, *Biomaterials* 2011, 32, 2204-2212.
7. E. C. Wu, S. Zhang, C. A. E. Hauser, *Advanced Functional Materials* 2012, 22, 456-468.
8. Y. Loo, Y.-C. Wong, E. Z. Cai, C.-H. Ang, A. Raju, A. Lakshmanan, A. G. Koh, H. J. Zhou, T.-C. Lim, S. M. Moochhala, C. A. E. Hauser, *Biomaterials* 2014, 35, 4805-4814.
9. Y. Loo, M. Goktas, A. B. Tekinay, M. O. Guler, C. A. Hauser, A. Mitraki, *Adv Healthc Mater* 2015, 4, 2557-2586.
10. Y. Loo, Y. S. Chan, I. Szczerbinska, B. C. P. Tan, A. C. A. Wan, H. H. Ng, C. A. E. Hauser, *ACS Applied Bio Materials* 2019, 2, 1406-1412.
11. H. H. Susapto, D. Alhattab, S. Abdelrahman, Z. Khan, S. Alshehri, K. Kahin, R. Ge, M. Moretti, A.-H. Emwas, C. A. E. Hauser, *Nano Letters* 2021, 21, 2719-2729.
12. W. Arab, C. A. E. Hauser, in *Peptide-based Biomaterials*, The Royal Society of Chemistry, 2021, pp. 363-394.
13. K. Autumn, Y. A. Liang, S. T. Hsieh, W. Zesch, W. P. Chan, T. W. Kenny, R. Fearing, R. J. Full, *Nature* 2000, 405, 681-685.
14. M. D. Bartlett, A. B. Croll, D. R. King, B. M. Paret, D. J. Irschick, A. J. Crosby, *Advanced Materials* 2012, 24, 994-994.
15. R. J. Stewart, T. C. Ransom, V. Hlady, *J Polym Sci B Polym Phys* 2011, 49, 757-771.
16. A. Hagenau, M. H. Suhre, T. R. Scheibel, *Progress in Polymer Science* 2014, 39, 1564-1583.
17. J. Yu, W. Wei, E. Danner, R. K. Ashley, J. N. Israelachvili, J. H. Waite, *Nature Chemical Biology* 2011, 7, 588-590.
18. A. F. Dexter, A. S. Malcolm, A. P. Middelberg, *Nat Mater* 2006, 5, 502-506.
19. M. de Loos, B. L. Feringa, J. H. van Esch, *European Journal of Organic Chemistry* 2005, 2005, 3615-3631.
20. X. Yan, D. Xu, X. Chi, J. Chen, S. Dong, X. Ding, Y. Yu, F. Huang, *Adv Mater* 2012, 24, 362-369.
21. M. Ikeda, T. Tanida, T. Yoshii, I. Hamachi, *Advanced Materials* 2011, 23, 2819-2822.
22. T. Aida, E. W. Meijer, S. I. Stupp, *Science* 2012, 335, 813-817.
23. H. Lee, S. M. Dellatore, W. M. Miller, P. B. Messersmith, *Science* (New York, N.Y.) 2007, 318, 426-430.
24. Q. Lin, D. Gourdon, C. Sun, N. Holten-Andersen, T. H. Anderson, J. H. Waite, J. N. Israelachvili, *Proc Natl Acad Sci USA* 2007, 104, 3782-3786.
25. J. D. White, J. J. Wilker, *Macromolecules* 2011, 44, 5085-5088.
26. H. Zhao, J. H. Waite, *J Biol Chem* 2006, 281, 26150-26158.
27. M. V. Rapp, G. P. Maier, H. A. Dobbs, N. J. Higdon, J. H. Waite, A. Butler, J. N. Israelachvili, *Journal of the American Chemical Society* 2016, 138, 9013-9016.
28. M. Shin, J. Y. Shin, K. Kim, B. Yang, J. W. Han, N.-K. Kim, H. J. Cha, *Journal of Colloid and Interface Science* 2020, 563, 168-176.
29. J. Yang, M. A. Cohen Stuart, M. Kamperman, *Chemical Society Reviews* 2014, 43, 8271-8298.
30. B. K. Ahn, S. Das, R. Linstadt, Y. Kaufman, N. R. Martinez-Rodriguez, R. Mirshafian, E. Kesselman, Y. Talmon, B. H. Lipshutz, J. N. Israelachvili, J. H. Waite, *Nature Communications* 2015, 6, 8663-8663.
31. M. Krogsgaard, M. A. Behrens, J. S. Pedersen, H. Birkedal, *Biomacromolecules* 2013, 14, 297-301.
32. Q. Zhao, D. W. Lee, B. K. Ahn, S. Seo, Y. Kaufman, J. N. Israelachvili, J. H. Waite, *Nat Mater* 2016, 15, 407-412.
33. Q. Zhao, D. W. Lee, B. K. Ahn, S. Seo, Y. Kaufman, Jacob N. Israelachvili, J. H. Waite, *Nature Materials* 2016, 15, 407-412.
34. J. Li, A. D. Celiz, J. Yang, Q. Yang, I. Wamala, W. Whyte, B. R. Seo, N. V. Vasilyev, J. J. Vlassak, Z. Suo, D. J. Mooney, *Science* 2017, 357, 378-381.
35. Y. Shou, J. Zhang, S. Yan, P. Xia, P. Xu, G. Li, K. Zhang, J. Yin, *ACS Biomaterials Science & Engineering* 2020, 6, 3619-3629.
36. L. Han, X. Lu, K. Liu, K. Wang, L. Fang, L.-T. Weng, H. Zhang, Y. Tang, F. Ren, C. Zhao, G. Sun, R. Liang, Z. Li, *ACS Nano* 2017, 11, 2561-2574.

37. Y. Zhou, L. Kang, Z. Yue, X. Liu, G. G. Wallace, *ACS Applied Bio Materials* 2020, 3, 628-638.
38. C. E. Brubaker, H. Kissler, L.-J. Wang, D. B. Kaufman, P. B. Messersmith, *Biomaterials* 2010, 31, 420-427.
39. R. Wang, J. Li, W. Chen, T. Xu, S. Yun, Z. Xu, Z. Xu, T. Sato, B. Chi, H. Xu, *Advanced Functional Materials* 2017, 27, 1604894.
40. C. J. Kastrup, M. Nahrendorf, J. L. Figueiredo, H. Lee, S. Kambhampati, T. Lee, S.-W. Cho, R. Gorbatov, Y. Iwamoto, T. T. Dang, P. Dutta, J. H. Yeon, H. Cheng, C. D. Pritchard, A. J. Vegas, C. D. Siegel, S. MacDougall, M. Okonkwo, A. Thai, J. R. Stone, A. J. Coury, R. Weissleder, R. Langer, D. G. Anderson, *Proceedings of the National Academy of Sciences* 2012, 109, 21444-21449.
41. L. Zhang, M. Liu, Y. Zhang, R. Pei, *Biomacromolecules* 2020, 21, 3966-3983.
42. F. Pan, S. Ye, R. Wang, W. She, J. Liu, Z. Sun, W. Zhang, *Materials Horizons* 2020, 7, 2063-2070.
43. B. D. B. Tiu, P. Delparastan, M. R. Ney, M. Gerst, P. B. Messersmith, *ACS Appl Mater Interfaces* 2019, 11, 28296-28306.
44. Y. Li, J. Cheng, P. Delparastan, H. Wang, S. J. Sigg, K. G. DeFrates, Y. Cao, P. B. Messersmith, *Nature Communications* 2020, 11, 3895.
45. M. Moretti, C. Canale, M. Francardi, S. Dante, F. De Angelis, E. Di Fabrizio, *Microsc Res Tech* 2012, 75, 1723-1731.
46. M. Moretti, R. La Rocca, M. Perrone Donnorso, B. Torre, C. Canale, M. Malerba, G. Das, R. Sottile, C. Garofalo, A. Achour, K. Kane, E. Carbone, E. Di Fabrizio, *ACS Nano* 2021, 15, 7500-7512.
47. Y. Loo, A. Lakshmanan, M. Ni, L. L. Toh, S. Wang, C. A. Hauser, *Nano Lett* 2015, 15, 6919-6925.
48. J. L. Hutter, J. Bechhoefer, *Journal of Vacuum Science & Technology B: Microelectronics and Nanometer Structures Processing, Measurement, and Phenomena* 1994, 12, 2251-2253.
49. A. L. Weisenhorn, P. K. Hansma, T. R. Albrecht, C. F. Quate, *Applied Physics Letters* 1989, 54, 2651-2653.
50. H. R. Nelson, A. H. Altieri, *Coral Reefs* 2019, 38, 177-198.
51. S. Schmidt-Roach, C. M. Duarte, C. A. E. Hauser, M. Aranda, *Frontiers in Marine Science* 2020, 7.
52. D. W. dela Cruz, B. Rinkevich, E. D. Gomez, H. T. Yap, *Ecological Engineering* 2015, 84, 408-415.
53. S. A. Schopmeyer, D. Lirman, E. Bartels, D. S. Gilliam, E. A. Goergen, S. P. Griffin, M. E. Johnson, C. Lustic, K. Maxwell, C. S. Walter, *Coral Reefs* 2017, 36, 1047-1057.
54. J. L. Huffer, J. Bechhoefer, *Review of Scientific Instruments* 1993, 64, 1868-1873.
55. W. L. Jorgensen, J. Tirado-Rives, *Proceedings of the National Academy of Sciences of the United States of America* 2005, 102, 6665-6670.
56. M. J. Abraham, T. Murtola, R. Schulz, S. Páll, J. C. Smith, B. Hess, E. Lindahl, *SoftwareX* 2015, 1-2, 19-25.
57. L. S. Dodda, I. Cabeza de Vaca, J. Tirado-Rives, W. L. Jorgensen, *Nucleic Acids Research* 2017, 45, W331-W336.
58. T. Darden, D. York, L. Pedersen, *The Journal of Chemical Physics* 1993, 98, 10089-10092.
59. H. J. C. Berendsen, J. P. M. Postma, W. F. v. Gunsteren, A. DiNola, J. R. Haak, *The Journal of Chemical Physics* 1984, 81, 3684-3690.
60. G. Bussi, D. Donadio, M. Parrinello, *The Journal of Chemical Physics* 2007, 126, 014101.
61. Y. J. Choi, Y. J. Jun, D. Y. Kim, H. G. Yi, S. H. Chae, J. Kang, J. Lee, G. Gao, J. S. Kong, J. Jang, W. K. Chung, J. W. Rhie, D. W. Cho, *Biomaterials* 2019, 206, 160-169.
62. A. Micsonai, F. Wien, É. Bulyáki, J. Kun, É. Moussong, Y.-H. Lee, Y. Goto, M. Refregiers, J. Kardos, *Nucleic Acids Research* 2018, 46, W315-W322.
63. W. Kabsch, C. Sander, *Biopolymers* 1983, 22, 2577-2637.
64. N. J. Greenfield, *Nat Protoc* 2006, 1, 2876-2890.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, products specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

While the present disclosure has been disclosed with references to certain embodiments, numerous modifications, alterations, and changes to the described embodiments are possible without departing from the sphere and scope of the present disclosure, as defined in the appended claims. Accordingly, it is intended that the present disclosure is not limited to the described embodiments, but that it has the full scope defined by the language of the following claims, and equivalents thereof.

What is claimed is:

1. An ultrashort peptide comprising a sequence selected from the group consisting of:

DopaIIZK, (SEQ ID NO: 1)

IIZDopaK, (SEQ ID NO: 2)

IIZKDopa, (SEQ ID NO: 3)

IIZ(KDopa)$_2$, and (SEQ ID NO: 4)

IIZ(KDopa)$_3$, (SEQ ID NO: 5)

wherein I is isoleucine, L is leucine, K is lysine, Z is cyclohexylalanine, and Dopa is levodopa.

2. The ultrashort peptide recited in claim 1, wherein amino acids in the peptide are either L-amino acids or D-amino acids.

3. The ultrashort peptide recited in claim 1, wherein the ultrashort peptide is capable of self-assembling into a hydrogel.

4. The ultrashort peptide recited in claim 1, wherein the ultrashort peptide may be optionally connected to an N-terminal protecting group and may be amidated or non-amidated by a C-terminal protecting group.

5. An ultrashort peptide consisting of a sequence selected from the group consisting of:

DopaIIZK, (SEQ ID NO: 1)

IIZDopaK, (SEQ ID NO: 2)

IIZKDopa, (SEQ ID NO: 3)

IIZ(KDopa)$_2$, and (SEQ ID NO: 4)

IIZ(KDopa)$_3$, (SEQ ID NO: 5)

wherein I is isoleucine, L is leucine, K is lysine, Z is cyclohexylalanine, and Dopa is levodopa.

6. An ultrashort peptide consisting of a sequence selected from the group consisting of:

DopaIIZK, (SEQ ID NO: 1)

IIZDopaK, (SEQ ID NO: 2)

IIZKDopa, (SEQ ID NO: 3)

IIZ(KDopa)$_2$, (SEQ ID NO: 4)

IIZ(KDopa)$_3$, (SEQ ID NO: 5)

wherein I is isoleucine, L is leucine, K is lysine, Z is cyclohexylalanine, and Dopa is levodopa and wherein each of the sequences may be optionally connected to an N-terminal protecting group and may be amidated or non-amidated by a C-terminal protecting group.

7. The ultrashort peptide recited in claim 4, wherein the N-terminal protecting group is a peptidomimetic molecule and wherein a N-terminus of the peptidomimetic molecule may be modified with a functional group.

8. The ultrashort peptide recited in claim 4, wherein the C-terminal protecting group is a small molecule or a linker.

9. The ultrashort peptide recited in claim 4, wherein the C-terminal protecting group is a functional group.

10. The ultrashort peptide recited in claim 1, wherein the ultrashort peptide has a gelation concentration of at least 1 mg/mL.

11. A gel comprising the ultrashort peptide recited in claim 1.

12. The gel of claim 11, wherein the gel is characterized by a loss factor tan δ (G"/G')<1.

13. The gel of claim 11, wherein the gel is characterized by a storage modulus G' of at least 2 kPa.

14. The gel of claim 11, comprising fibers of the peptide of claim 1, the fibers defining a network that is capable of entrapping at least one of a microorganism, a virus particle, a peptide, a peptoid, a protein, a nucleic acid, an oligosaccharide, a polysaccharide, a vitamin, an inorganic molecule, a synthetic polymer, a micro- or nanoparticle, a small organic molecule or a pharmaceutically active compound.

15. The gel of claim 11, wherein the gel is adhesive.

16. The gel of claim 11, wherein the gel has an adhesion force of at least 5 pN per 150 $nm^2$ surface area.

17. A method of preparing a gel, the method comprising:
    dissolving an ultrashort peptide recited in claim 1 in an aqueous or buffer solution or an organic solution, respectively.

18. The method of claim 17, wherein the buffer solution is saline or phosphate buffered saline.

19. The method of claim 17, wherein the ultrashort peptide is dissolved at a concentration of at least 1 mg/mL.

20. A 2D or 3D cell culture substrate comprising the gel of claim 11.

21. A gel comprising the ultrashort peptide recited in claim 6.

22. The gel of claim 21, wherein the gel is biocompatible.

\* \* \* \* \*